United States Patent
Yoshida et al.

(10) Patent No.: US 9,539,375 B2
(45) Date of Patent: *Jan. 10, 2017

(54) INTEGRATED LEUKOCYTE, OXYGEN AND/OR $CO_2$ DEPLETION, AND PLASMA SEPARATION FILTER DEVICE

(71) Applicant: New Health Sciences, Inc., Bethesda, MD (US)

(72) Inventors: Tatsuro Yoshida, West Newton, MA (US); Paul J. Vernucci, Billerica, MA (US)

(73) Assignee: New Health Sciences, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/635,560

(22) Filed: Mar. 2, 2015

(65) Prior Publication Data
US 2015/0165102 A1 Jun. 18, 2015

Related U.S. Application Data

(63) Continuation of application No. 13/572,412, filed on Aug. 10, 2012, now Pat. No. 9,005,343, which is a
(Continued)

(51) Int. Cl.
*B01D 19/00* (2006.01)
*B01D 53/22* (2006.01)
(Continued)

(52) U.S. Cl.
CPC ......... *A61M 1/0268* (2013.01); *A61M 1/0209* (2013.01); *A61M 1/0213* (2014.02);
(Continued)

(58) Field of Classification Search
CPC ......... B01D 19/00; B01D 53/22; B01D 61/00; B01D 2257/104; A61M 1/0209; A61M 1/0213; A61M 1/0218; A61M 1/0272; A61M 1/0281; A61M 1/34; A61M 1/3633; A61M 1/3679; A61M 1/38; A61M 2202/2008; A61M 2202/0225; A61M 2202/0415; A61M 2202/0439; A61M 1/0268
(Continued)

(56) References Cited

U.S. PATENT DOCUMENTS

| 4,086,924 A | 5/1978 | Latham, Jr. |
| 4,228,032 A | 10/1980 | Talcott |

(Continued)

FOREIGN PATENT DOCUMENTS

| CN | 2894710 Y | 5/2007 |
| DE | 3722984 | 1/1989 |

(Continued)

OTHER PUBLICATIONS

Alcantar et al., "Polyethylene glycol-coated biocompatible surfaces," *Journal of Biomedical Materials Research*, 51(3):343-351 (2000).
(Continued)

*Primary Examiner* — Jason M Greene
(74) *Attorney, Agent, or Firm* — Arnold & Porter LLP

(57) ABSTRACT

A blood filter device comprising: a housing comprising an outer wall and a first inlet, a first outlet and a second outlet; a membrane which is capable of separating plasma from the blood, wherein the membrane forms an inner chamber; a leukocyte and oxygen and/or carbon dioxide depletion media disposed wherein the inner chamber, the leukocyte and oxygen and/or carbon dioxide depletion media is capable of depleting leukocytes and oxygen and/or carbon dioxide from the blood; an outer chamber disposed between
(Continued)

the outer wall and the membrane, wherein the plasma which permeates through the membrane enters the outer chamber and exits the filter device via the first outlet; whereby the blood which has been depleted of oxygen and/or carbon dioxide, leukocytes and plasma exists and filter device via the second outlet.

20 Claims, 12 Drawing Sheets

Related U.S. Application Data continuation-in-part of application No. 12/901,350, filed on Oct. 8, 2010, now Pat. No. 8,535,421.

(60) Provisional application No. 61/522,168, filed on Aug. 10, 2011, provisional application No. 61/522,157, filed on Aug. 10, 2011, provisional application No. 61/331,693, filed on May 5, 2010.

(51) Int. Cl.
A61M 1/02 (2006.01)
A61M 1/34 (2006.01)
A61M 1/36 (2006.01)
A61M 1/38 (2006.01)

(52) U.S. Cl.
CPC ........ A61M 1/0218 (2014.02); A61M 1/0272 (2013.01); A61M 1/0281 (2013.01); A61M 1/34 (2013.01); A61M 1/3633 (2013.01); A61M 1/3679 (2013.01); A61M 1/38 (2013.01); A61M 2202/0208 (2013.01); A61M 2202/0225 (2013.01); A61M 2202/0415 (2013.01); A61M 2202/0427 (2013.01); A61M 2202/0429 (2013.01); A61M 2202/0439 (2013.01)

(58) Field of Classification Search
USPC ..... 96/4, 6, 8, 108, 153, 154; 95/46, 51, 54; 604/4.01, 5.01, 5.04, 6.01, 6.15; 435/2; 206/524.6
See application file for complete search history.

(56) References Cited

U.S. PATENT DOCUMENTS

| | | |
|---|---|---|
| 4,300,559 A | 11/1981 | Gajewski et al. |
| 4,370,160 A | 1/1983 | Ziemelis |
| 4,381,775 A | 5/1983 | Nose' et al. |
| 4,540,416 A | 9/1985 | Hattori et al. |
| 4,572,899 A | 2/1986 | Walker et al. |
| 4,585,735 A | 4/1986 | Meryman et al. |
| 4,629,544 A | 12/1986 | Bonaventura et al. |
| 4,654,053 A | 3/1987 | Sievers et al. |
| 4,670,013 A | 6/1987 | Barnes et al. |
| 4,701,267 A | 10/1987 | Watanabe et al. |
| 4,713,176 A | 12/1987 | Schoendorfer et al. |
| 4,748,121 A | 5/1988 | Beaver et al. |
| 4,749,551 A | 6/1988 | Borgione |
| 4,769,175 A | 9/1988 | Inoue |
| 4,769,318 A | 9/1988 | Hamasaki et al. |
| 4,837,047 A | 6/1989 | Sato et al. |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 5,000,848 A | 3/1991 | Hodgins et al. |
| 5,023,054 A | 6/1991 | Sato et al. |
| 5,037,419 A | 8/1991 | Valentine et al. |
| 5,139,668 A | 8/1992 | Pan et al. |
| 5,152,905 A | 10/1992 | Pall et al. |
| 5,192,320 A | 3/1993 | Anazawa et al. |
| 5,208,335 A | 5/1993 | Ramprasad et al. |
| 5,229,012 A | 7/1993 | Pall et al. |
| 5,254,248 A | 10/1993 | Nakamura et al. |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,476,764 A | 12/1995 | Bitensky |
| 5,506,141 A | 4/1996 | Weinreb et al. |
| 5,529,821 A | 6/1996 | Ishikawa et al. |
| 5,605,934 A | 2/1997 | Giertych |
| 5,617,873 A | 4/1997 | Yost et al. |
| 5,624,794 A | 4/1997 | Bitensky et al. |
| 5,635,358 A | 6/1997 | Wilding et al. |
| 5,691,452 A | 11/1997 | Gawryl et al. |
| 5,693,230 A | 12/1997 | Asher |
| 5,698,250 A | 12/1997 | DelDuca et al. |
| 5,730,989 A | 3/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,811,142 A | 9/1998 | DelDuca et al. |
| 5,846,427 A | 12/1998 | Kessler et al. |
| 5,895,810 A | 4/1999 | Light et al. |
| 5,902,747 A | 5/1999 | Nemser et al. |
| 5,972,710 A | 10/1999 | Weigl et al. |
| 6,027,623 A | 2/2000 | Ohkawa |
| 6,045,701 A | 4/2000 | Ung-Chhun et al. |
| 6,047,203 A | 4/2000 | Sackner et al. |
| 6,090,062 A | 7/2000 | Sood et al. |
| 6,148,536 A | 11/2000 | Iijima |
| 6,150,085 A | 11/2000 | Hess et al. |
| 6,156,231 A | 12/2000 | McKedy |
| 6,162,396 A | 12/2000 | Bitensky et al. |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,482,585 B2 | 11/2002 | Dottori |
| 6,527,957 B1 | 3/2003 | Deniega et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,723,051 B2 | 4/2004 | Davidson et al. |
| 6,761,695 B2 | 7/2004 | Yost et al. |
| 6,773,407 B2 | 8/2004 | Yost et al. |
| 6,817,979 B2 | 11/2004 | Nihtilä |
| 6,866,783 B2 | 3/2005 | Baurmeister et al. |
| 6,899,822 B2 | 5/2005 | McKedy |
| 6,955,648 B2 | 10/2005 | Mozayeni et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |

(56) References Cited

U.S. PATENT DOCUMENTS

| | | |
|---|---|---|
| 7,452,601 B2 | 11/2008 | Ebner et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,763,097 B2 | 7/2010 | Federspiel |
| 7,775,376 B2 | 8/2010 | Bonaguidi et al. |
| 8,071,282 B2 | 12/2011 | Bitensky et al. |
| 9,005,343 B2 * | 4/2015 | Yoshida ............ A61M 1/0209 206/524.6 |
| 2001/0027156 A1 | 10/2001 | Egozy et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0168982 A1 | 9/2004 | Bitensky et al. |
| 2005/0038342 A1 | 2/2005 | Mozayeni et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2007/0078113 A1 | 4/2007 | Roth et al. |
| 2007/0240569 A1 | 10/2007 | Ooya |
| 2008/0027368 A1 | 1/2008 | Kollar et al. |
| 2008/0160107 A1 | 7/2008 | McCaney et al. |
| 2008/0243045 A1 | 10/2008 | Pasqualini |
| 2008/0276803 A1 | 11/2008 | Molaison et al. |
| 2009/0017128 A1 | 1/2009 | Monzyk et al. |
| 2009/0269837 A1 | 10/2009 | Shevkoplyas et al. |
| 2010/0221697 A1 | 9/2010 | Sehgal |
| 2010/0313755 A1 | 12/2010 | Koros et al. |
| 2010/0331767 A1 | 12/2010 | Frankowski |
| 2012/0024156 A1 | 2/2012 | Yoshida et al. |
| 2012/0077182 A1 | 3/2012 | Bitensky et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0219633 A1 | 8/2012 | Sowemimo-Coker |
| 2013/0004937 A1 | 1/2013 | Yoshida et al. |
| 2013/0259744 A1 | 10/2013 | Yoshida et al. |
| 2013/0327677 A1 | 12/2013 | McDorman |

FOREIGN PATENT DOCUMENTS

| | | |
|---|---|---|
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1 109 447 B1 | 10/2003 |
| EP | 1 891 999 A1 | 2/2008 |
| FR | 2 581 289 A1 | 11/1986 |
| GB | 1 044 649 A2 | 10/1966 |
| JP | 58-194879 | 11/1983 |
| JP | 63-63616 A | 3/1988 |
| JP | 01-104271 A | 4/1989 |
| JP | 5-305123 A | 11/1993 |
| JP | 06-121920 A | 5/1994 |
| JP | 2700170 B2 | 1/1998 |
| JP | 2000-516963 A | 12/2000 |
| JP | 2002-253936 A | 9/2002 |
| JP | 2004/089495 | 3/2004 |
| JP | 2005-535279 A | 11/2005 |
| JP | 2007-260393 A | 10/2007 |
| JP | 10/501443 | 2/2010 |
| KR | 10-0721054 | 5/2006 |
| SU | 1718766 A1 | 1/1990 |
| WO | WO 81/02239 A1 | 8/1981 |
| WO | WO 86/00809 A1 | 2/1986 |
| WO | WO 89/02274 A1 | 3/1989 |
| WO | WO 91/04659 A1 | 4/1991 |
| WO | WO 92/08348 A1 | 5/1992 |
| WO | WO 95/29662 A2 | 11/1995 |
| WO | WO 96/29103 A1 | 9/1996 |
| WO | WO 96/29346 A1 | 9/1996 |
| WO | WO 96/29864 A1 | 10/1996 |
| WO | WO 97/37628 A1 | 10/1997 |
| WO | WO 99/25726 A1 | 5/1999 |
| WO | WO 99/48963 A2 | 9/1999 |
| WO | WO 03/043419 A1 | 5/2003 |
| WO | WO 03/043571 A2 | 5/2003 |
| WO | WO 03/086577 A1 | 10/2003 |
| WO | WO 2006/057473 A1 | 6/2006 |
| WO | WO 2011/014855 A2 | 2/2011 |
| WO | WO 2011/046841 A1 | 4/2011 |
| WO | WO 2011/046963 A1 | 4/2011 |
| WO | WO 2012/027582 A1 | 3/2012 |
| WO | WO 2012/061731 A1 | 5/2012 |

OTHER PUBLICATIONS

Anderson et al., "Microfabrication and microfluidics for tissue engineering: state of the art and future opportunities," *Lab Chip*, 4:98-103 (2004).

Barbee et al., "The Fahraeus Effect," *Microvascular Research*, 3:6-16 (1971).

Barclay et al., "A Method for Detecting Chaos in Canine Myocardial Microcirculatory Red Cell Flux," *Microcirculation*, 7(5):335-346 (2000).

Bardy et al., "Technetium-99m Labeling by Means of Stannous Pyrophosphate: Application to Bleomycin and Red Blood Cells," *Journal of Nuclear Medicine*, 16(5):435-437 (1975).

Barras et al., "Einfluss der Rejuvenation auf die rheologischen Eigenschaften gelagerter Erythrozyten," *VASA*, 23(4):305-311 (1994).

Beutler et al., "Storage of red cell concentrates in CPD-A2 for 42 and 49 days," *The Journal of Laboratory and Clinical Medicine*, 102(1):53-62 (1983).

Borenstein et al., "Microfabrication Technology for Vascularized Tissue Engineering," *Biomedical Microdevices*, 4(3):167-175 (2002).

Brody et al., "Deformation and Flow of Red Blood Cells in a Synthetic Lattice: Evidence for an Active Cytoskeleton," *Biophysical Journal*, 68:2224-2232 (1995).

Burns et al., "Artificial microvascular network: a new tool for measuring rheologic properties of stored red blood cells," *Transfusion*, 52(5):1010-1023 (2012).

Carmen, "The Selection of Plastic Materials for Blood Bags," *Transfusion Medicine Reviews*, 7(1):1-10 (1993).

Can et al., "Nonlinear Dynamics of Microvascular Blood Flow," *Annals of Biomedical Engineering*, 28:641-652 (2000).

Cell Deformability, RheoSCAN (RheoScan-AnD300/RheoScan-D300), obtained on Dec. 11, 2012, from: http://www.rheoscan.com/products/products-01.html.

Chilton et al., "Privacy Protection of Health Information: Patient Rights and Pediatrician Responsibilities," *Pediatrics*, 104(4):973-977 (1999).

Cokelet et al., "Fabrication of in Vitro Microvascular Blood Flow Systems by Photolithography," *Microvascular Research*, 46:394-400 (1993).

Dale et al., "Human Vaccination with *Escherichia coli* J5 Mutant Induces Cross-Reactive Bactericidal Antibody against *Neisseria*

(56) References Cited

OTHER PUBLICATIONS gonorrhoeae Lipooligosaccharide," *The Journal of Infectious Diseases*, 166:316-325 (1992).
De Angelis et al., "Erythrocyte Shape Control in Stored Blood: The Effect of Additive Solutions on Shape Recovery," *Haematologica*, 73:7-12 (1988).
De Venuto et al., "Rejuvenation of Human Red Blood Cells During Liquid Storage," *Transfusion*, 14(4):338-344 (1974).
Deible et al., "Molecular barriers to biomaterial thrombosis by modification of surface proteins with polyethylene glycol," *Biomaterials*, 19:1885-1893 (1998).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumaswala et al., "Studies in Red Blood Cell Preservation: 9. The Role of Glutamine in Red Cell Preservation," *Vox Sang*, 67:255-259 (1994).
Dumont et al., "Anaerobic storage of red blood cells in a novel additive solution improves in vivo recovery," *Transfusion*, 49(3):458-464 (2009).
Durapore® Membrane Filters—Filter Discs and Membranes, retrieved on Aug. 26, 2014, from: www.emdmillipore.com/US/en/product/Durapore.
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
European Search Report completed on Feb. 11, 2005, in European Patent Application No. 02 78 2307.9.
Extended European Search Report, dated Aug. 8, 2014 for European Patent Application No. 10823965.8.
Extended European Search Report, dated Oct. 23, 2014 for European Patent Application No. 11838889.1.
Extended European Search Report dated Nov. 4, 2014 in European Patent Application No. 12807324.4.
Extended European Search Report, dated Mar. 5, 2015 in European Patent Application No. 12821624.9.
Fahraeus et al., "The Viscosity of the Blood in Narrow Capillary Tubes," *Am. J. Physiol.*, 96(3):562-568 (1931).
Fang et al., "Inhibition of Lipopolysaccharide-Associated Endotoxin Activities In Vitro and In Vivo by the Human Anti-Lipid A Monoclonal Antibody SdJ5-1.17.15," *Infection and Immunity*, 61(9):3873-3878 (1993).
Frame et al., "A System for Culture of Endothelial Cells in 20-50-µm Branching Tubes," *Microcirculation*, 2(4):377-385 (1995).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gifford et al., "A detailed study of time-dependent changes in human red blood cells: from reticulocyte maturation to erythrocyte senescence," *British Journal of Haematology*, 135:395-404 (2006).
Gifford et al., "Parallel Microchannel-Based Measurements of Individual Erythrocyte Areas and Volumes," *Biophysical Journal*, 84:623-633 (2003).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).

Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Hamasaki et al., "Acid-citrate-dextrose-phosphoenolpyruvate medium as a rejuvenant for blood storage," *Transfusion*, 23(1):1-7 (1983).
Hess et al., "Successful storage of RBCs for 9 weeks in a new additive solution," *Transfusion*, 40:1007-1011 (2000).
Hess, "Extended Liquid Storage of Red Blood Cells," Blood Donors and the Supply of Blood and Blood Products, National Academy Press, Washington, D.C., pp. 99-102 (1996).
Hess, "Storage of red blood cells under anaerobic conditions," *Vox Sanguinis*, 93:183 (2007).
Hodgson et al., "Prophylactic use of human endotoxin-core hyperimmune gammaglobulin to prevent endotoxaemia in colostrum-deprived, gnotobiotic lambs challenged orally with *Escherichia coli,*" *FEMS Immunology and Medical Microbiology*, 11:171-180 (1995).
Högman et al.,"Effects of Oxygen on Red Cells during Liquid Storage at +4° C," *Vox Sang.*, 51:27-34 (1986).
Högman et al., "Cell Shape and Total Adenylate Concentration as Important Factors for Posttransfusion Survival of Erythrocytes," *Biomed. Biochim. Acta*, 42:S327-S331 (1983).
Högman et al., "Effects of Oxygen and Mixing on red cells stored in plastic bags at +4° C," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Holme et al., "Current Issues Related to the Quality of Stored RBC's," *Transfusion and Apheresis Science, Elsevier Science*, 33(1):55-61 (2005).
Huang et al., "Continuous Particle Separation Through Deterministic Lateral Displacement," *Science*, 304:987-990 (2004).
International Search Report completed on Apr. 26, 2011, in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Feb. 8, 2011, in International Patent Application No. PCT/US10/52084.
International Search Report completed on Jul. 10, 2014 in International Patent Application No. PCT/US2014/019537.
International Search Report completed on Jul. 8, 1996, in International Patent Application No. PCT/US96/09005.
International Search Report completed on Jun. 18, 2012, in International Patent Application No. PCT/US12/30930.
International Search Report completed on May 20, 2010, in International Patent Application No. PCT/US2010/31055.
International Search Report completed on Nov. 10, 2003, in International Patent Application No. PCT/US02/36735.
International Search Report completed on Nov. 22, 2010, in International Patent Application No. PCT/US2010/052376.
International Search Report completed on Nov. 9, 2012, in International Patent Application No. PCT/US12/45426.
International Search Report completed on Sep. 24, 2012, in International Patent Application No. PCT/US12/50380.
Jain, et al., "Determinants of Leukocyte Margination in Rectangular Microchannels," *PLoS ONE*, 4(9):1-8 (2009).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).

(56) References Cited

OTHER PUBLICATIONS

Kaihara et al., "Silicon Micromachining to Tissue Engineer Branched Vascular Channels for Liver Fabrication," *Tissue Engineering*, 6(2):105-117 (2000).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Koch et al., "Duration of Red-Cell Storage and Complications After Cardiac Surgery," *The New England Journal of Medicine*, 358:1229-1239 (2008).
Koch et al., "Peripheral blood leukocyte NO production and oxidative stress in multiple sclerosis," *Multiple Sclerosis*, 14:159-165 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Extending the storage of red cells at 4° C," *Transfus. Sci.*, 15(2):105-115 (1994).
Meryman et al., "Prolonged storage of red cells at 4° C," *Transfusion*, 26(6):500-505 (1986).
Moll et al., "Dean vortices applied to membrane process. Part II: Numerical approach," *Journal of Membrane Science*, 288:321-335 (2007).
Moroff et al., "Proposed standardization of methods for determining the 24-hour survival of stored red cells," *Transfusion*, 24:109-114 (1984).
Murphy et al., "Increased Mortality, Postoperative Morbidity, and Cost After Red Blood Cell Transfusion in Patients Having Cardiac Surgery," *Circulation*, 116:2544-2552 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Poxton, "Antibodies to lipopolysaccharide," *Journal of Immunological Methods*, 186:1-15 (1995).
Prefiltration before membrane filtration, hydrophobic, 25 μm 142 mm, retrieved on Aug. 26, 2014, from: www.emdmillipore.com/US/en/product/Prefiltration-before-membrane-filtration.
Pries et al., "Biophysical aspects of blood flow in the microvasculature," *Cardiovascular Research*, 32:654-667 (1996).
Sambuceti et al., "Why should we study the coronary microcirculation?," *Am J Physiol Heart Circ Physiol*, 279:H2581-H2584 (2000).
Shevkoplyas et al., "Direct measurement of the impact of impaired erythrocyte deformability on microvascular network perfusion in a microfluidic device," *Lab Chip*, 6:914-920 (2006).

Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Supplementary European Search Report dated Jan. 20, 2015 in European Patent Application No. 12822378.2.
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," Transfusion, 41:550-555 (2001).
The International Committee for Standardization in Hematology, "Recommended Methods for Radioisotope Red Cell Survival Studies," *Blood*, 38(3):378-386 (1971).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C in additive solution (AS-1, AS-3, or AS-5) for 42 days and then biochemically modified, frozen, thawed, washed, and stored at 4° C in sodium chloride and glucose solution for 24 hours," *Transfusion*, 40:1341-1345 (2000).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely Injured: Does Age of Transfused Blood Affect Outcomes?," *The Journal of TRAUMA*, 65(4):794-798 (2008).
Wilding et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion*, 7(6):401-408 (1967).
Wu et al., "Polymer microchips bonded by $O_2$-plasma activation," *Electrophoresis*, 23:782-790 (2002).
Yoshida et al., "Anaerobic storage of red blood cells," *Blood Transfusion*, 8:220-236 (2010).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).

* cited by examiner

INTEGRATED LEUKOCYTE, OXYGEN AND/OR $CO_2$ DEPLETION, AND PLASMA SEPARATION FILTER DEVICE

RELATED APPLICATIONS

This application is a continuation of U.S. application Ser. No. 13/572,412, filed on Aug. 10, 2012 (pending), which claims priority to U.S. Provisional Application No. 61/522,168 entitled "Integrated Leukocyte, Oxygen and/or CO2 Depletion, and Plasma Separation Filter Device," filed Aug. 10, 2011 and to U.S. Provisional Application No. 61/522,157 entitled "Leukoreduction and Oxygen Depletion Device," filed Aug. 10, 2011, and is a Continuation-In-Part of U.S. patent application Ser. No. 12/901,350, filed on Oct. 8, 2010, entitled "Blood Storage Bag System and Depletion Devices with Oxygen and Carbon Dioxide Depletion Capabilities," now U.S. Pat. No. 8,535,421, issued on Sep. 17, 2013, which claims the benefit of U.S. Provisional Application No. 61/331,693 filed on May 5, 2010, each of which are herein incorporated by reference in their entireties.

FIELD OF THE DISCLOSURE

The present disclosure generally relates to and includes an integrated leukocyte, oxygen and/or $CO_2$ depletion, and plasma separation filter device. More particularly, the present disclosure relates to and includes the prolonged anaerobic storage of packed red blood cells in liquid form from collection from a donor to transfusion to a recipient using this integrated leukocyte, oxygen and/or $CO_2$ depletion, and plasma separation filter device.

BACKGROUND OF THE DISCLOSURE

The supplies of liquid blood are currently limited by storage systems used in conventional blood storage practice. Using current systems, stored blood expires after a period of about 42 days of refrigerated storage at a temperature above freezing (i.e., 4° C.) as packed blood cell preparations. Expired blood cannot be used and must be discarded because it will harm the ultimate recipient. One of the primary reasons for blood spoilage is its continued metabolic activity after it is stored. For example, in 2007, more than 45 million units of packed red blood cells (pRBC) were collected and stored globally (15.6 million in US). During refrigerated storage, all of these pRBC became progressively damaged by storage lesions. When transfused within the current 6-week limit, stored pRBC have lower quality (fraction of pRBC removed; compromised $O_2$ delivery capacity) as well as potential toxicity, often manifested as side effects of transfusion therapy. These storage lesions are observed as altered biochemical and physical parameters associated with stored cells. Examples of these in vitro measured parameters include reduced metabolite levels (ATP and 2,3-DPG), reduced surface area, echinocytosis, phosphatidylserine exposure, and reduced deformability.

Human red blood cells (RBC) in vivo are in a dynamic state. In whole blood, white blood cells are normally present in the range between 4,300 and 10,800 cells/μL and the normal RBC range at sea level is 5.4 million/μL (±0.8) for men and 4.8 million μL (±0.6) for women. The red blood cells contain hemoglobin, the iron-containing protein that carries oxygen throughout the body and gives red blood its color.

Stored blood undergoes steady deterioration which is partly caused by hemolysis, hemoglobin degradation and reduced adenosine triphosphate (ATP) concentration that occur during the storage period. These reasons and others limit the amount of readily available high quality blood needed for transfusions.

When pRBC are stored at 1-6° C. (standard storage condition) in a blood storage bag, away from mechanical stress and the constantly cycling environment of the circulation, the senescence process is partially suspended. However, with the lack of constant nutrient replenishment and waste removal under refrigerated storage, pRBC are gradually damaged, resulting in compromised physiological functions. The following problems occur during extended storage:

a. When pRBC are stored for an extended period, storage lesions accumulate and deteriorate pRBC and cause the up to 1% of pRBC to be hemolyzed during storage and up to 25% to be removed shortly after transfusion.

b. Non-viable pRBC cause iron overload in chronically transfused patients.

c. Transfusion does not always achieve the intended outcome of increased tissue perfusion.
   Hemoglobin in pRBC do not release oxygen efficiently at tissues due to loss of 2,3-DPG.
   pRBC are not able to enter and perfuse capillary beds due to loss of deformability.

Transfusing pRBC stored for longer periods may result in higher morbidity and longer hospital stays compared to transfusing "fresher" red cells.

Higher morbidity and longer hospital stays result with pRBC that are stored longer than 2-3 weeks, in comparison to fresher red cells. For example, negative clinical outcomes in cardiac surgery occur when using 'older' blood; multiple organ failure in surgical patients reflecting the age of transfused red cells; correlation between older units and increased mortality in severe sepsis; failure to improve $O_2$ utilization attributed to decreased 2,3-DPG and decreased cardiac index associated with increased blood viscosity This evidence suggests that the ineffectiveness and negative consequences of transfusion is attributable at least in part to the compromising effects of extended storage of pRBC. In addition to immediate removal by the recipient of certain pRBC, consequences of pRBC storage lesions include: (i) Depletion of ATP (loss of RBC's ability to dilate the pre-capillary arteriole); (ii) Depletion of 2,3-DPG; (iii) Accumulation of oxidative damage caused by reactive oxygen species (ROS) formed by the reaction of denatured hemoglobin with $O_2$; and (iv) Decreased pRBC deformability and increased pRBC viscosity—caused in part by oxidative damage to membrane and cytoskeleton. Less deformable pRBC are excluded from capillary channels resulting in low capillary occupancy and reduced tissue perfusion. Massive transfusion of undeformable cells may also contribute to multiple organ failure by blocking the organs' capillary beds. After transfusion, 2,3-DPG is synthesized relatively quickly in vivo to ~50% of the normal level in as little as 7 hours and to ~95% of the normal level in 2-3 days. However, since 2,3-DPG-depleted cells do not recover their levels immediately, $O_2$-carrying capacity is compromised to the detriment of critically ill patients requiring immediate $O_2$ delivery and tissue perfusion. There are numerous reports that emphasize the importance of pRBC with high oxygen carrying capacity in such clinical situations.

Packed red blood cells (pRBC) prepared from whole blood or from apheresis techniques currently undergo sequential processing to deplete plasma, leukocytes and oxygen. This results in increased processing time and loss of red blood cells.

The present disclosure overcomes the disadvantages of the conventional sequential processing of red blood cells via the development of a filter device that combines all three depletion steps into a single integrated device.

SUMMARY OF THE DISCLOSURE

The present disclosure provides for and includes a blood filter device having a housing with an outer wall, an inlet, a first outlet and a second outlet, a membrane capable of separating plasma from blood forming an inner chamber, a leukocyte and $O_2$ depletion media in an inner chamber, an outer chamber between the outer wall and membrane to collect plasma permeating through the membrane and exiting through a first outlet and a second outlet for collecting leukocyte and $O_2$ depleted packed red blood cells from the inner chamber.

The present disclosure further provides for and includes a blood filter device having a housing with an outer wall, an inlet, a first outlet and a second outlet, a membrane capable of separating plasma from blood forming an inner chamber, a leukocyte, $O_2$ and $CO_2$, depletion media in an inner chamber, an outer chamber between the outer wall and membrane to collect plasma permeating through the membrane and exiting through a first outlet and a second outlet for collecting leukocyte and $O_2$ depleted packed red blood cells from the inner chamber.

The present disclosure further provides for and includes a blood filter device having a housing with an outer wall, an inlet, a first outlet and a second outlet, a membrane capable of separating plasma from blood forming an inner chamber, a leukocyte, $O_2$, $CO_2$, and platelet depletion media in an inner chamber, an outer chamber between the outer wall and membrane to collect plasma permeating through the membrane and exiting through a first outlet and a second outlet for collecting leukocyte and $O_2$ depleted packed red blood cells from the inner chamber.

The disclosure further provides for and includes an integrated filter device which comprises a filter media that is capable of depleting both oxygen and/or $CO_2$ and leukocytes, while allowing plasma to permeate through a portion of the filter media, thereby producing concentrated or packed red blood cells and separated plasma.

The disclosure further provides for and includes a blood filter device comprising: a housing comprising an outer wall and first and second end caps, wherein the first end cap comprises an inlet and the second end cap comprises at least a first and second outlet; a membrane which is capable of separating plasma from the blood, wherein the membrane forms an inner chamber; a leukocyte and oxygen/carbon dioxide depletion media disposed wherein the inner chamber, the leukocyte and oxygen/carbon dioxide depletion media is capable of depleting leukocytes and oxygen and/or carbon dioxide from the blood; an outer chamber disposed between the outer wall and the membrane, wherein the plasma which permeates through the membrane enters the outer chamber and exits the filter device via the first outlet; whereby the blood which has been depleted of oxygen and/or carbon dioxide, and leukocytes, as well as separated from plasma exits the filter device via the second outlet.

DETAILED DESCRIPTION

Definitions

Figure 1:
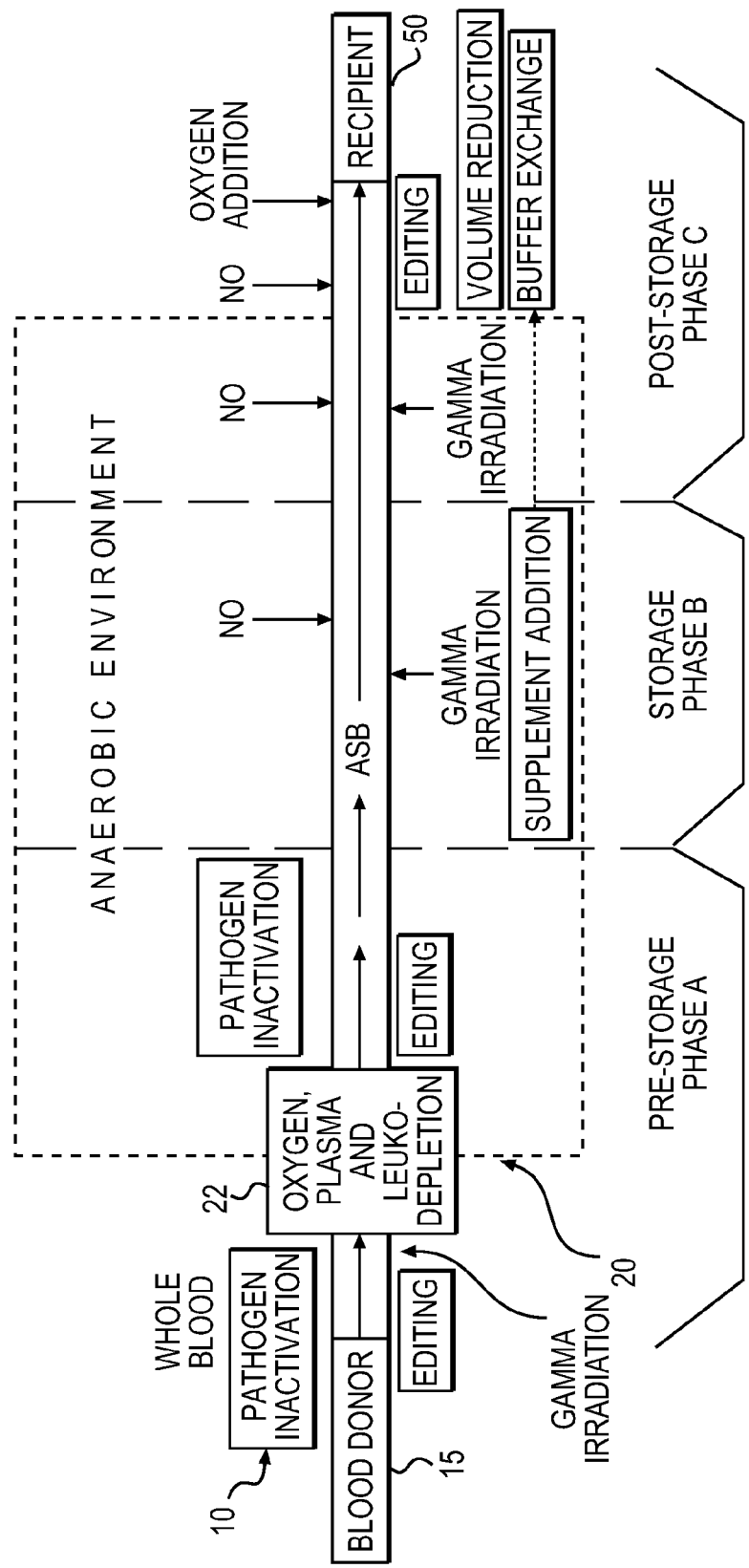
FIG. 1 illustrates a flowchart of the components and processing steps from blood collection to transfusion using a disposable blood anaerobic storage system including an integrated leukocyte, oxygen/carbon dioxide depletion and plasma separation filter device according to the present disclosure.
Figure 2:
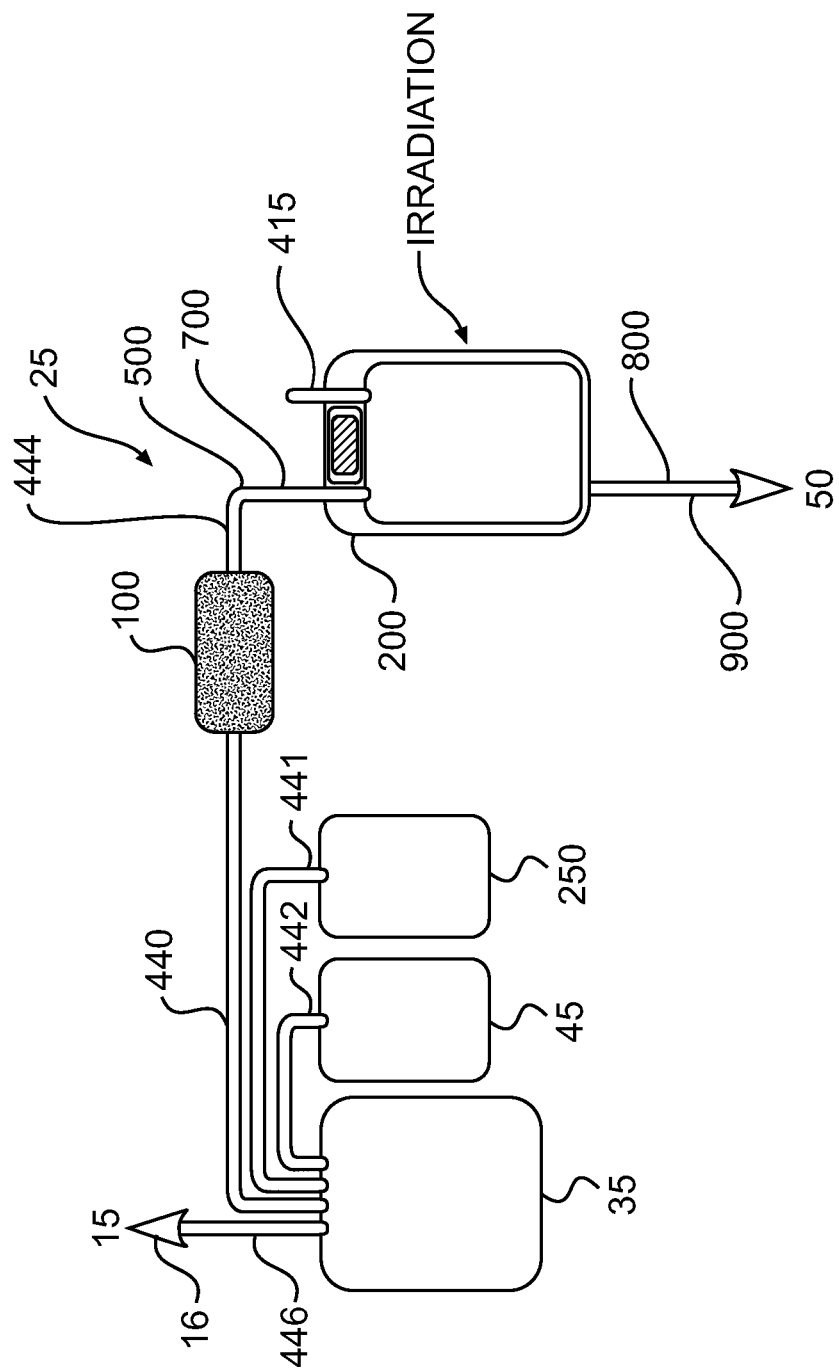
FIG. 2 is a schematic representation of an exemplary system including a leukoreduction filter/oxygen removal/ $CO_2$ device according to the present disclosure.

Whole Donor Blood Whole blood is preferably donated from a healthy individual or donor 15 and held in a blood bank for later use to be ultimately used by a recipient 50. Patients who are scheduled for surgery may donate blood for themselves in a process known as autologous blood donation. Alternatively, blood is donated for use by another in a process known as heterologous transfusion.

Whole Blood Whole blood is a suspension of blood cells that contains red blood cells, white blood cells, platelets suspended in a fluid called plasma, containing electrolytes, hormones, vitamins and antibodies.

Depleted Blood As used herein, depleted blood refers to blood depleted of one or more components found in either whole donor blood or whole blood. Depleted blood includes blood depleted of $O_2$, $CO_2$, leukocytes, platelets, cell fragments, iron or free heme. Depleted blood is prepared by the removal of components directly or indirectly by filtration, binding, and sparging. Depleted blood may optionally include additives, including for example, anticoagulants, sugars, buffers, salts, or ATP. Exemplary additives are described in U.S. application Ser. No. 10/295,781, filed Nov. 15, 2002, entitled "Additive Solution for Blood Preservation", herein incorporated by reference in its entirety.

Packed Red Blood Cells (pRBC) The percentage of blood volume composed of red blood cells is called the hematocrit. Packed Red Blood Cells are cells obtained from whole blood or whole donor blood that have an increased hematocrit relative the whole blood or whole donor blood starting material. Packed red blood cells (pRBC) may be prepared from whole blood using centrifugation techniques commonly known in the art. Packed red blood cells may also be prepared using filtration methods. The packed red blood cells are the blood component that will be stored in the unique storage system of this disclosure for later transfusion.

Packed red blood cells may contain additive solution. Packed red blood cells can also be collected by apheresis techniques such that components are separated during collection.

Anaerobic and Oxygen Depleted Terms anaerobic and oxygen depleted are used interchangeable throughout this application and refer an environment for pRBCs and plasma in which the presence of oxygen is actively reduced to a low oxygen level by the treatment with oxygen sorbent and then maintained in the presence of oxygen sorbent. In other aspects, the presence of oxygen may be actively reduced to a low oxygen level by the treatment with oxygen sorbent and then maintained in oxygen impermeable storage containers, for example a storage bag. Exemplary storage bags may be found, for example, in U.S. application Ser. No. 12/901,350, filed Oct. 8, 2010, entitled "Blood Storage Bag System and Depletion Devices with Oxygen and Carbon Dioxide Depletion Capabilities," and hereby incorporate by reference in its entirety. Anaerobic and oxygen depleted are used in reference to oxygen depletion devices and oxygen storage throughout the present disclosure. Carbon dioxide may also be depleted from anaerobic or oxygen depleted pRBC.

The normal life span of a RBC is 120 days. Approximately 0.875% of the RBCs are retired every 24 hours by the spleen and new RBCs are made by the bone marrow. Consequently, when blood is drawn from a donor, there are a spectrum of cells of different ages.

A function of RBC is to exchange oxygen and carbon dioxide at lung and tissues, and unlike other cells in body, it does not rely on oxygen in oxidative phosphorylation but entirely on glycolysis for ATP production. ATP is critical for viability of RBC and together with 2,3-DPG, their free cytosolic concentrations are tightly regulated by their function on feedback inhibition to key enzymes in glycolytic pathway. Under refrigerated storage condition, dis-inhibition of glycolytic pathway is desirable to overcome the gradual depletion of ATP and 2,3-DPG over several weeks of storage. Hemoglobin concentration in RBC is similar to 2,3-DPG and ATP, and its deoxygenated state has a binding pocked with high affinities for 2,3-DPG and ATP compared to oxy-hemoglobin. Thus, stripping this oxygen to few % occupancy (~60% occupied when collected and processed) will cause uptake of 2,3-DPG and ATP, resulting in reduced concentration of free molecules, stimulating glycolytic flux.

Platelets The platelets are small cellular components of blood that facilitate the clotting process by sticking to the lining of the blood vessels. The platelets, like the red blood cells, are made by the bone marrow and survive in the circulatory system for 9 to 10 days before they are removed by the spleen. Platelets are typically prepared using a centrifuge to separate the platelets from the plasma.

Plasma Plasma is a protein-salt solution and the liquid portion of the blood in which red and white blood cells and platelets are suspended. Plasma is 90% water and constitutes about 55 percent of the blood volume. One of the primary functions of plasma is to assist in blood clotting and immunity. Plasma is obtained by separating the liquid portion of the blood from the cells. Typically, plasma is separated from the cells by centrifugation. Centrifugation is the process used to separate the components of the whole blood into the plasma, the white blood cells, the platelets and the packed red blood cells. In some cases, the plasma will initially fractionate to the top of a vessel during a light spin. This light fraction is then removed from the vessel and plasma and platelets are separated and harvested by further centrifugations. In some cases white blood cells and platelets are removed by a leuko reduction filter to produce leukoreduced pRBC. The present disclosure provides an efficient alternative to using a centrifuge that minimizes the cost of traditionally used instrumentation.

Editing Editing pRBC is the process of identifying and removing blood cells that have a poor likelihood of surviving the transfusion process or will likely die shortly after transfusion. Editing dead or dying red blood cells may be employed by using, for example, a filter-like device. In some aspects, editing can be very important because a leading cause of morbidity and mortality to transfused patients is the non-viable portion of the blood that is transfused independent of any pathogen transmission. The importance of editing increases with the increasing age of stored blood product.

The present disclosure includes and provides for in one aspect an integrated system and method for the preparation and extended storage of packed red blood cells (pRBC), from receipt of whole blood from a donor until transfusion to a recipient, as shown in FIG. 1 and as described by flowchart, and referenced by reference numeral 10. Flowchart 10 describes a system 20 that includes an additive addition, oxygen, carbon dioxide or oxygen and carbon dioxide depletion of pRBC before and during storage, together with treatments include leukoreduction, editing, pathogen reduction, irradiation and nitric oxide (NO) treatment and oxygen addition to enhance the quality of stored pRBC and to optimize the transfusion process to a recipient and reduce morbidity associated with such transfusion.

Referring to the drawings, and particular to FIG. 1, a flowchart 10 describes blood storage system 20 from collection from a donor 15 to transfusion to a recipient 50. System 20 shows a process that has three phases during which different sub-processes or steps occur. The three phases are Pre-storage Phase A, Storage Phase B and Post-storage Phase C. Significantly, different steps of the blood storage process 20 can occur at different phases to achieve optimal blood transfusion results. For example, gamma irradiation can optionally occur during Pre-storage Phase A before oxygen and/or carbon dioxide depletion and plasma separation 22, during Storage Phase B or during the Post-storage Phase C. Storage Phase B and portion of Pre-storage Phase A and Post storage Phase C, significantly occur during an anaerobic environment. Similarly, editing can occur during Pre-storage Phase A or during Post-storage Phase C. Significantly, the anaerobic phase includes the entire Storage Phase, the anaerobic portion of Phase A and the anaerobic portion of Phase C. The anaerobic environment has synergistic relationships with steps such as the addition of nitric oxide, gamma irradiation and pathogen inactivation that provide significant advantages to the RBCs that must occur in such anaerobic environment, as will be discussed below. Accordingly, there exist several different sequences for the blood storage process.

Pre-storage Phase A is the time from collection from a donor to storage in an anaerobic environment. During Phase A, whole blood is collected from donor 15, and the blood components, namely, plasma, platelets and RBCs are separated. Steps such as pathogen inactivation, leukoreduction and editing also occur during Pre-storage Phase A. During Phase A, oxygen, plasma and leukocytes are depleted prior to Storage Phase B.

Storage Phase B is an entirely anaerobic period during which the oxygen, plasma and leukocyte depleted pRBC are stored in an anaerobic environment, e.g., a sealed bag.

Post-storage Phase C, occurs prior to transfusion to recipient 50. Accordingly, steps such as the volume reduction, editing, cleansing during buffer exchange, the addition of either or both nitric oxide or nitric oxide precursors and oxygen occur during this phase. These steps are significant because the recipient is likely to already be in a compromised condition, therefore the pRBC must be prepared to be accepted by the recipient in an optimal condition.

The length of time of a phase or subphase should typically be as short as possible. In one aspect, a phase or subphase is less than 2, 3, 4, 5, 10, 20, 30, 40, 50, or 60 minutes. In another aspect, a phase or subphase is less than 30 minutes, 1 hour, 2 hours, 3 hours or 5 hours. In a further aspect, a phase or subphase is between 2 to 5 minutes, 5 to 10 minutes, 10 to 20 minutes or 20 to 30 minutes.

A method may be designed using a device or devices disclosed herein that adopts combination of the steps described herein.

The present disclosure provides for and includes a blood filter device having a housing with an outer wall, an inlet, a first outlet and a second outlet, a membrane capable of separating plasma from blood forming an inner chamber, a leukocyte and $O_2$ depletion media in an inner chamber, an outer chamber between the outer wall and membrane to collect plasma permeating through the membrane and exiting through a first outlet and a second outlet for collecting leukocyte and $O_2$ depleted packed red blood cells from the inner chamber.

Figure 3:
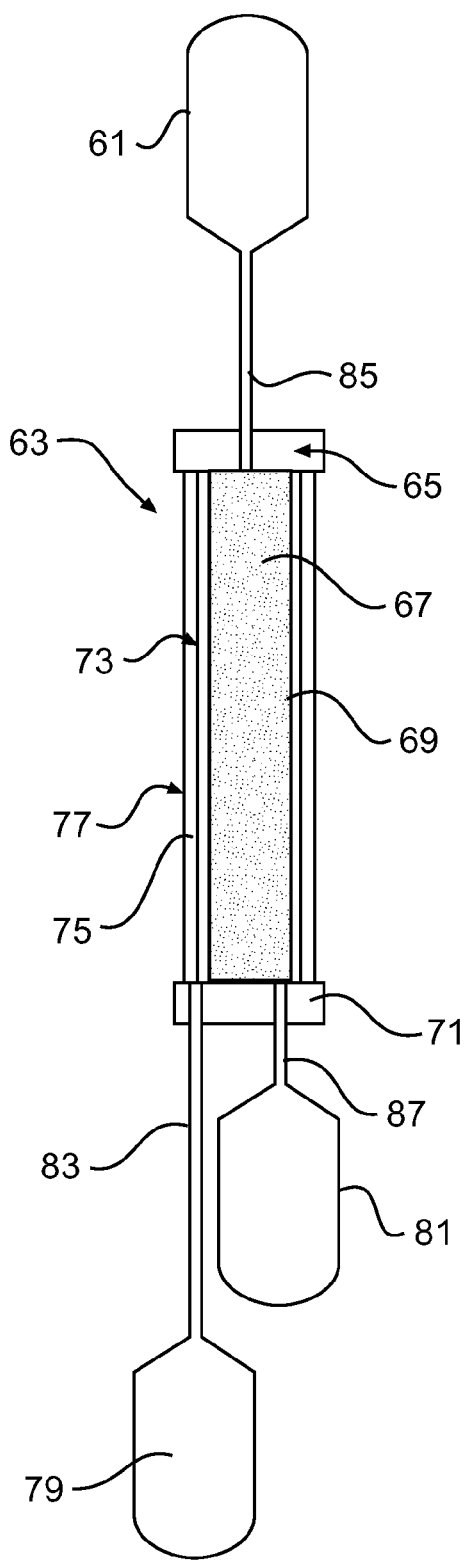
FIG. 3 is a schematic representation of an exemplary integrated leukocyte, oxygen/carbon dioxide depletion and plasma separation filter device according to the present disclosure.

An example of an integrated leukocyte, oxygen and plasma depletion filter device may be shown and understood by referring to FIG. 3, wherein whole blood (unpacked red blood cells) from container or bag 61 enters integrated leukocyte, oxygen and plasma depletion filter device 63 via device inlet chamber 65 wherein the red blood cells come into contact with leukoreduction/oxygen/carbon dioxide depletion media 67 disposed within inner chamber 69. As the red blood cells migrate from device inlet chamber 65 through inner chamber 69 and exits via device outlet chamber 71, the leukocytes and oxygen and/or carbon dioxide are depleted from the treated unpacked red blood cells from bag 61. Simultaneously, plasma is separated from the unpacked red blood cells as it traverses through inner chamber 69 and contacts at least one hydrophilic microporous membrane 73. Thereafter, the separated plasma is removed from leukocyte, oxygen and/or carbon dioxide, and plasma separation filter device 63 via a conduit 75 disposed between hydrophilic microporous membrane 73 and outer chamber 77, and thereafter stored in plasma container or bag 79. The oxygen and/or carbon dioxide, leukocyte and plasma depleted packed red blood cells are thereafter removed from filter device 63 via device outlet chamber 71 and thereafter stored in container or bag 81.

Leukocyte/oxygen and/or carbon dioxide depletion media 67 may comprise a macroporous structure designed to allow unpacked red blood cells to flow through the filter pores with minimal adhesion, while leukocytes are removed by adsorption and/or size exclusion. Structures according the present disclosure may be formed from fibrous or foam materials that can be organic or inorganic in nature. The surface chemistry of these structures may be altered to promote leukocyte adhesion. In some aspects, the structures may not be designed to react with or absorb oxygen and/or carbon dioxide present in the pRBC product.

In aspects according to the present disclosure, a housing may be prepared from either a rigid or a flexible material. In certain aspects, the outer wall of a housing may be prepared from a thermoplastic material. In an aspect a housing may be prepared from polyethylene, polypropylene, polystyrene, polyvinyl chloride, and polytetrafluoroethylene (PTFE). In an aspect, the housing may be prepared from Eastar™ copolyester. In an aspect, a housing may be prepared from a thermosetting polymer. In aspects according to the present disclosure, a thermosetting polymer may be Bakelite™, Duroplast, Melamine, and epoxy resin, polyimides, cyanate esters or polycyanurates. The present disclosure provides for and includes housings having one or more openings. In certain aspects, the blood filter device may have a first inlet that provides for the entrance of blood into the device. In an aspect, the first inlet may also serve as an outlet that provides for the removal of the depleted blood. In an aspect, the blood may enter through a first inlet into the housing where the flow is facilitated by the presence of a vacuum. In another aspect, the first inlet may also serve as an outlet to provide for the escape of gas from the device as the blood enters the device. In an aspect, the first inlet may serve as an outlet to provide for the recovery of depleted blood.

Housings of the present disclosure having one or more openings may have a first inlet and a first outlet. In an aspect, the first inlet provides for the entrance of the blood into the device while the first outlet provides for the escape of gas or air displaced from the device by the entering whole blood or whole donor blood. In an aspect, the first outlet may further provide for the flow of the depleted blood from the blood filter device. In other aspects, the depleted blood may be recovered from the first inlet. In further aspects of the current disclosure, the housing having one or more openings may have a first inlet, a first outlet and a second outlet. In some aspects, the first or second outlet may provide for the escape of displaced gas from the device. In some aspects, the first outlet may provide for the flow of filtered plasma from an outer chamber of the device. In other aspects, the first outlet may provide for the flow of filtered plasma from an inner chamber of the device. In an aspect, the filtered plasma flowing from either a first outlet or a second outlet may be depleted of one or more of $O_2$, $CO_2$, leukocytes, platelets, cell fragments, iron and free heme.

In aspects according to the present disclosure, the first outlet and second outlet may provide for the flow of separated blood components. In an aspect, the device provides for the separation of the housing into an inner chamber and an outer chamber. In an aspect, the first outlet may provide for the flow of plasma from an outer chamber of a blood filter device. In another aspect, the first outlet may provide for the flow of plasma from an inner chamber of a blood filter device. In some aspects, the first outlet provides for the flow of pRBCs from blood filter device and the second outlet provides for the flow of plasma. In other aspects according the present disclosure, the blood components flowing from the first and second outlets may be depleted blood. Inlets and outlets according the present disclosure may be connected to standard tubing used during blood collection including PVC blood tubing, 0.160" OD.

The present disclosure also includes and provides for seals connected to the first inlet, first outlet, second outlet or combinations thereof. Examples of exemplary seals are provided in Jorgensen et al., U.S. Pat. No. 6,439,577, issued Aug. 27, 2002, entitled "Rotating Seals for Cell Processing Systems" and Latham, Jr. U.S. Pat. No. 4,086,924, issued May 2, 1978, entitled "Plasmapheresis Apparatus", each of which are hereby incorporated by reference in their entireties.

Included and provided for in the present disclosure are devices having a membrane or membranes which is capable of separating plasma from blood. In aspects according to the present disclosure, a membrane may be a hydrophilic microporous membrane. Referring to FIG. 3, a membrane may be a hydrophilic microporous membrane 73 that may surround the leukocytes/oxygen and/or carbon dioxide depletion media 67 which may form inner chamber 69 inside of filter device 63. The downstream side of hydrophilic microporous membrane 73 may be connected to container 79 via a conduit 83. Container 79 and conduit 83 may impart a negative pressure on the downstream side of hydrophilic microporous membrane 73 as does container 81 connected to the upstream side of membrane 73 which may be used to collect the packed or concentrated anaerobic red blood cells. Containers 79 and 81 may be positioned in a manner sufficient to control the hydrostatic differential pressure across hydrophilic microporous membrane 73, resulting in a method of controlling the concentration factor of the red blood cells.

In aspects according the present disclosure, the membrane may form one or more inner chambers within the housing. In an aspect, a membrane forms an inner chamber where the blood enters the inner chamber and plasma permeates through the membrane from the inner chamber to an outer chamber. Exemplary aspects of devices of the present disclosure are illustrated in the figures as described below.

Membrane or filter material may contain an oxygen and/or carbon dioxide absorbing material in the bulk of the filter media mass that has the capacity to bind oxygen and/or carbon dioxide present in a unit of pRBC. The oxygen and/or carbon dioxide absorbing materials may have the outer surface modified to increase biocompatibility and leukocyte adhesion, while allowing diffusion of oxygen and/or carbon dioxide through the outer surface into the inner mass for binding. Surface modifications may include radiation grafting, graft polymerization, polymer coating or encapsulation, or standard wet chemistry polymer derivatization methods.

In an aspect, inner chamber 69 may be separated from outer chamber 77 by at least one membrane 73. In an aspect the membrane may be a hydrophilic microporous membrane 73. Membrane 73 may allow plasma to flow into outer chamber 77, but retain red blood cells. Plasma flow rate may be enhanced by rotating inner chamber 69 within outer chamber 77 or by rotating outer chamber 77 around inner chamber 69 to reduce the boundary layer that could develop. The plasma collected in outer chamber 77 may flow into device outlet chamber 71, conduit 83 and then may be collected in collection bag 79. The depleted concentrated red blood cells may flow into device outlet chamber 71, conduit 87 and then into pRBC collection bag 81.

Membrane 73 may be formed from at least one material selected from the group consisting of: PVDF rendered hydrophilic, nylon, cellulose esters, polysulfone, polyethersulfone, polypropylene rendered hydrophilic, and polyacrylonitrile. In aspects according to the present disclosure, the hydrophilic microporous membrane may be a multilayered membrane. In an aspect a multilayered membrane may have two or more materials a combination of selected from the group consisting of: PVDF rendered hydrophilic, nylon, cellulose esters, polysulfone, polyethersulfone, polypropylene rendered hydrophilic, and polyacrylonitrile. Membranes of the present disclosure may be further surface modified to control cell adhesion, protein binding and fouling. In some aspects, a membrane may be modified to increase the hydrophilicity. In an aspect, a polysulfone material may be combined with PVP to prepare membranes with increased hydrophilicity. In an aspect, the membrane may be prepared from polysulfone.

In an aspect according the present disclosure, the membrane 73 may be hydrophilic microporous membrane. In other aspects, membrane 73 may be formed from more than one hydrophilic microporous membrane. In some aspects, more than one membrane may be fused together. In other aspects, more than one membrane may be layered. In some aspects, the layered membranes may be separated by a media. In an aspect, the media may be a depletion media as provided below.

In aspects according to the present disclosure, the membrane may be less than 250 microns thick. In an aspect, the membrane may be greater than 25 microns thick. In some aspects the membrane may be between 25 and 250 microns thick. In other aspects, the membrane may be between 25 and 100 or 25 and 150 microns thick. In an aspect, the membrane may be between 50 and 100 microns thick, 75 and 100 microns thick, 50 and 150 microns thick, 75 and 150 microns thick, 100 and 250 microns thick, 150 and 250 microns thick or between 25 and 150 microns thick.

Membranes according the present disclosure include porous membranes. In certain aspects, the membrane may be microporous. In some aspects, the pores may be less than 2 microns in diameter. Micropores may be from 0.5 to 2 microns in diameter. In other aspects micropores may be from greater than 0.1 to 1.9 microns in diameter. In an aspect, the micropores may be greater than 0.2 and less than 2 microns. In another aspect, the micropores may be greater than 0.2 and less than 1.5 microns. In some aspects that micropores may be greater than 0.3 or 0.4 microns. In other aspects, the micropores may be greater than 0.5 or 0.6 microns.

A function of device according to the present disclosure may be illustrated by referring to FIG. 3, wherein whole blood from container 61 may flow into the device via first inlet chamber 65 via conduit 85. The whole blood may then flow through a leukocyte and oxygen depletion media 67 contained in inner chamber 69. In an aspect, the leukocyte and oxygen depletion media 67 may further provide for and include $CO_2$ depletion. In yet another aspect, the leukocyte and oxygen depletion media 67 may provide for platelet depletion. In some aspects, the leukocyte and oxygen depletion media binds and retains leukocytes and $O_2$. In other aspects the leukocyte and oxygen depletion media binds and retains leukocytes, $O_2$, and $CO_2$. In another aspect, the leukocyte and oxygen depletion media 67 may bind platelets and leukocytes from the whole blood and deplete $O_2$ from the red blood cells. In yet another aspect, the leukocyte and oxygen depletion media 67 may bind platelets and leukocytes from the whole blood and deplete $O_2$ and $CO_2$ from the red blood cells.

In aspects according to the present disclosure, $O_2$ depletion media may be materials that remove oxygen from RBCs or strip oxygen from the blood prior to storage. An oxygen scavenger can be used to remove the oxygen from the RBCs prior to storage in a blood bag. As used herein, "oxygen scavenger" or "oxygen sorbent" is a material that binds to or combines with $O_2$ under the conditions of use. The term "oxygen sorbent" may be used interchangeably herein with oxygen scavenger. In certain aspects according the present disclosure, a material may bind to or combines with oxygen irreversibly. In aspects according to the present disclosure, a material binds oxygen with higher affinity than hemoglobin. In other aspects, oxygen may bind to a sorbent material and have a very slow rate of release, $k_{off}$. In an aspect, the oxygen may chemically react with some component of the material and be converted into another compound. Any material where the off-rate of bound oxygen is much less than the residence time of the blood can serve as an oxygen scavenger. Non-limiting examples of oxygen scavengers include iron powders and organic compounds. Examples of $O_2$ sorbents include chelates of cobalt, iron, and Schiff bases.

Additional non-limiting examples for $O_2$ sorbents may be found in Bulow et al., U.S. Pat. No. 7,347,887, issued Mar. 25, 2008, entitled "Oxygen sorbent compositions and methods of using same"; Ramprasad, et al., U.S. Pat. No. 5,208,335, issued May 4, 1993, entitled "Reversible oxygen sorbent compositions"; and Sievers, et al., U.S. Pat. No. 4,654,053, issued Mar. 31, 1987, entitled "Oxygen Sorbent"; each of which is hereby incorporated by reference in their entireties. Oxygen sorbent materials may be formed into or incorporated in fibers, microspheres and foams.

In aspects according to the present disclosure, a sorbent may be an oxidizable organic polymer having a polymeric backbone and a plurality of pendant groups. Examples of sorbents with a polymeric backbone include a saturated hydrocarbon (<0.01% carbon-carbon double bonds). In some aspects, the backbone can contain monomers of ethylene or styrene. In an aspect, a polymeric backbone may be ethylenic. In another aspect, an oxidizable organic compound may be ethylene/vinyl cyclohexene copolymer (EVCH). Additional examples of substituted moieties and catalysts are provided in Yang et al., U.S. Patent Publication No. 2003/0183801, hereby incorporated by reference in its entirety. In additional aspects, an oxidizable organic polymer can also comprise substituted hydrocarbon moieties. Examples of oxygen scavenging polymers include those described by Ching et al., International Patent Publication WO99/48963, hereby incorporated by reference in its entirety. Oxygen scavenging materials may include those provided in Ebner et al., U.S. Pat. No. 7,754,798, issued Jul. 13, 2010, entitled "Oxygen scavenger block copolymers and compositions"; Ebner et al., U.S. Pat. No. 7,452,601 issued Nov. 18, 2008, entitled "Oxygen scavenger compositions derived from isophthalic acid/or terephthalic acid monomer or derivatives thereof"; Ebner et al., U.S. Pat. No. 6,387,461, issued May 14, 2002, entitled "Oxygen scavenger compositions"; each of which are hereby incorporated by reference in their entireties.

In aspects according the present disclosure, oxygen scavenger compositions can be used in the microparticles or microfibers. For example, oxygen scavenging particles can be included into conventional leukoreduction fibers made of PBT or PET as taught in Clauberg et al., U.S. Pat. No. 6,610,772, issued Aug. 26, 2003, entitled "Platelet Particle Polymer Composite with Oxygen Scavenging Organic Cations," hereby incorporated by reference in its entirety.

As used herein, "carbon dioxide scavenger" is a material that binds to or combines with carbon dioxide under the conditions of use. The term "carbon dioxide sorbent" may be used interchangeably herein with carbon dioxide scavenger. In certain aspects according the present disclosure, a material may bind to or combine with $CO_2$ irreversibly. In aspects according to the present disclosure, a material may bind $CO_2$ with higher affinity than hemoglobin. In other aspects, a sorbent material may bind $CO_2$ with high affinity such that the carbonic acid present in the blood or RBC cytoplasm is released and absorbed by the sorbent. In other aspects, $CO_2$ binds to a sorbent material and has a very slow rate of release, $k_{off}$. In an aspect, the carbon dioxide can chemically react with some component of the material and be converted into another compound. Carbon dioxide scavengers include metal oxides and metal hydroxides. Metal oxides react with water to produce metal hydroxides. The metal hydroxide reacts with carbon dioxide to form water and a metal carbonate. In an aspect, the carbon dioxide scavenger may be calcium oxide. For example, if calcium oxide is used, the calcium oxide will react with water that is added to the sorbent to produce calcium hydroxide

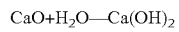

The calcium hydroxide will react with carbon dioxide to form calcium carbonate and water.

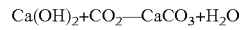

In certain aspects of the present disclosure, the depletion material may combine both $O_2$ and $CO_2$ depletion or scavenging activity. Non-limiting examples of $CO_2$ scavengers include oxygen scavengers and carbon dioxide scavengers provided by Multisorb Technologies (Buffalo, N.Y.). Oxygen scavengers may exhibit a secondary functionality of carbon dioxide scavenging.

In aspects according to the present disclosure, $O_2$ depletion media and $CO_2$ depletion media may be blended to a desired ratio to achieve desired results.

In aspects according to the present disclosure, sorbents can be formed inside the pores of porous micro glass fibers. The encapsulation of transition-metal complexes within the pores of a porous material may be achieved by using a ship-in-a-bottle synthesis in which the final molecule is prepared inside the pores by reacting smaller precursors. After the synthesis, the large molecule may remain 'mechanically entrapped' and encapsulated inside the pores with some restricted conformation and arrangement. A cobalt phthalocyanine/porous glass composite fiber for oxygen separation can be prepared by ship-in-a-bottle synthesis where encapsulation of cobalt phthalocyanine into pores of porous glass fibers is achieved by chemical vapour deposition using 1,2-dicyanobenzene. See, Kuraoka, et al., "Ship-in-a-bottle synthesis of a cobalt phthalocyanine/porous glass composite membrane for oxygen separation," Journal of Membrane Science, 286(1-2):12-14 (2006), herein incorporated by reference in its entirety.

In some aspects, porous glass fibers may manufactured as provided in Beaver et al., U.S. Pat. No. 4,748,121, issued entitled "Porous Glass Fibers with Immobilized Biochemically Active Material," herein incorporated by reference in its entirety. In another aspect, a sorbent can formed as a porous sheet product using papermaking/non-woven wet-laid equipment. Sheets with $O_2$ scavenging formulations may be as described in Inoue, U.S. Pat. No. 4,769,175, issued Sep. 6, 1988, entitled "Sheet-like, Oxygen-scavenging Agent," herein incorporated by reference in its entirety, can be formed and then encapsulated with a silicone film.

The lowest oxygen saturation may be achieved by using devices in which the sorbent is placed close to fibers to enable rapid diffusion time. Additional factors that increase oxygen and/or carbon dioxide diffusion are larger active surface area of fibers exposed to sorbent materials. The scavenging rates of oxygen scavengers may be limited by the surface area available for reaction with oxygen and how readily oxygen diffuses into the scavenger material. Surface area availability can be increased by incorporating the scavenger into microparticles or microfibers. Porous or micro-void structures also have increased surface areas available for reaction with oxygen.

In aspects according to the present disclosure, the sorbents may be prepared as a macroporous structure. In some aspects the macroporous structure may be a fibrous material, a foam or a microsphere. As used herein, a macroporous structure is a material or materials that is porous to particles of about 5 to 10 microns. A macroporous structure may be a weaved fiber, random fiber or a packed bed having layers, a packed bed having a heterogeneous mix of particles. Macroporous structures may include micro or macroparticles embedded or entrapped in a fibrous or foam structure.

In an aspect, the macroporous structure may further comprise a leukocyte binding surface. In another aspect, the macroporous structure may further comprise a platelet binding surface. In some aspects, the macroporous structure may be a mixture of separate $O_2$, leukocyte, $CO_2$, and platelet sorbent materials arranged together in combination. In an aspect, the macroporous structure may be a combination of sorbent materials in a single material. In one aspect, the macroporous structure may be a combined $O_2$ and leukocyte binding material arranged together with a $CO_2$ binding material to produce an $O_2$, leukocyte and $CO_2$ depleting macroporous structure. In another aspect, the macroporous structure may be a combined $O_2$ and $CO_2$ binding material coated with a leukocyte binding material to produce an $O_2$, leukocyte and $CO_2$ depleting macroporous structure.

In aspects according the present disclosure, the macroporous structure may provide for a flow of whole blood, whole donor blood or a fraction of either. In an aspect, the macroporous structure has a mean flow pore of between 10 and 30 microns. The mean flow pore may be determined using a porosymeter. Alternatively, the mean pore flow may be calculated for fibers and microspheres based on the geometry. In another aspect, the mean flow pore may be less than 30 microns. In another aspect, the mean flow pore may be 10 to 20 microns. In an aspect, the mean flow pore may be about 10 microns, about 15 microns, about 20 microns or about 25 microns. In other aspects, the mean flow pore may be between 15 and 25 microns. In yet another aspect, the mean flow pore may be 25 microns or less, 20 microns or less, or 15 microns or less.

In some aspects, the surface area of the macroporous structure may be a fiber having a surface area capable of removing $O_2$, $CO_2$, leukocytes, platelets or a combination thereof. In some aspects the surface area may be at least $5 \times 10^3$ cm²/g media. In an aspect the surface are may be from 10 cm² to 2000 cm². In another aspect, the surface are may be from 20 cm² to 1000 cm². For fibers, the surface area may be determined based on the diameter of the fiber. In certain aspects, the surface area may be determined empirically by the binding capacity of the leukocyte binding surface and the volume of blood to be depleted.

In an aspect, the fiber may have a bulk density of from 0.01 g/cm³ to 0.7 g/cm³ and has an average distance between adjacent fibers of between 7 μm to 300 μm. In an aspect, the bulk density of the fibers may be from 0.001 g/cm³ to 0.7 g/cm³. In another aspect, the bulk density of the fibers may be from 0.10 g/cm³ to 0.5 g/cm³. As used herein, the term "bulk density" means a numerical value expressed in g/cm3 obtained by dividing the weight (in gram) of the mass of fibers by the volume (in cm³) of the mass of fibers. Additional limitations and requirements for the requirements of leukocyte reduction filters may be found in Watanabe et al., U.S. Pat. No. 4,701,267, issued Oct. 20, 1987, entitled "Method for Removing Leukocytes," hereby incorporated by reference in its entirety.

Figure 5:
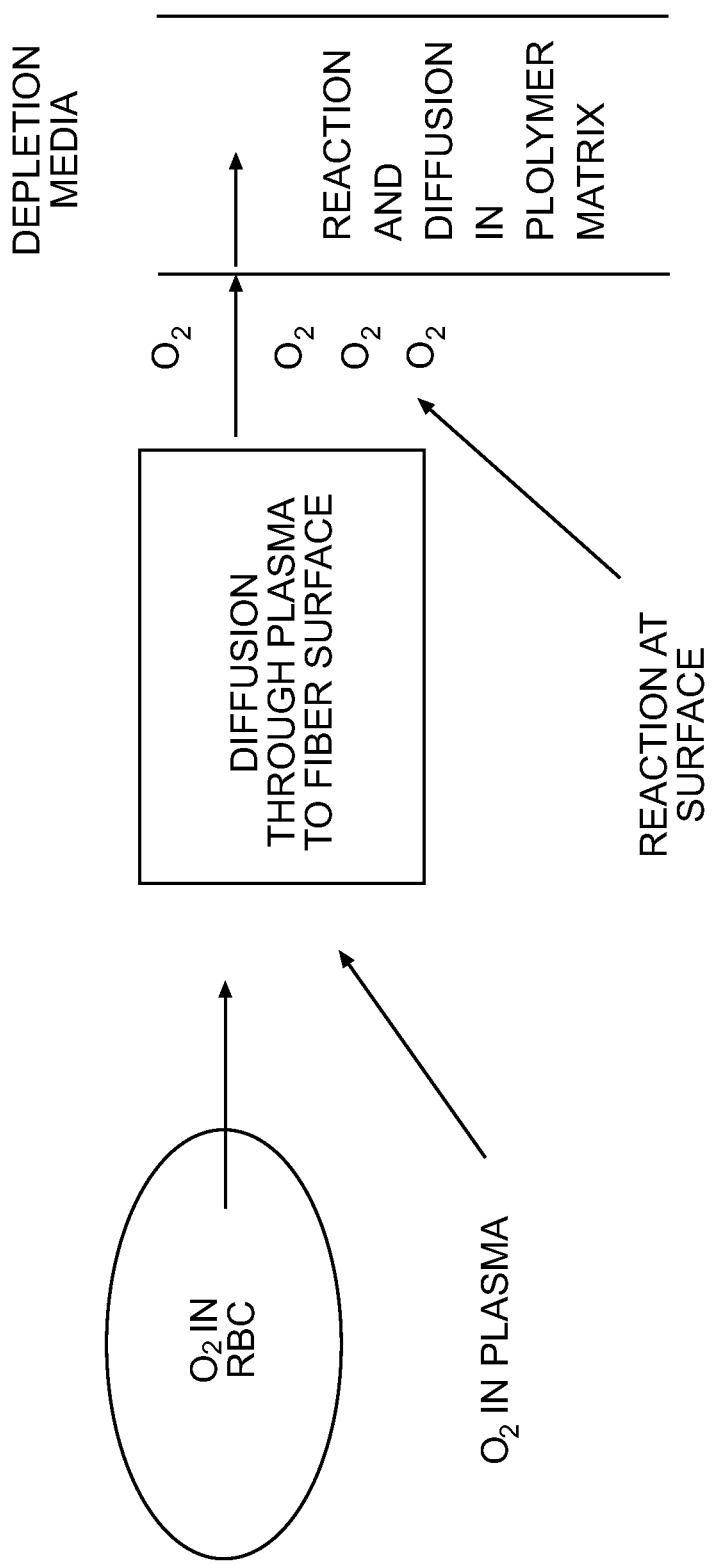
FIG. 5 illustrates the stepwise flow of $O_2$ during the process of depletion of $O_2$ from the RBC and plasma to absorption by a depletion media.

Removal of oxygen from packed red blood cells by a reactive filter involves a number of steps. Referring to FIG. 5, given the majority of the oxygen is bound to hemoglobin within the red blood cells, in order to remove the $O_2$, the oxygen needs to be released to the plasma. Oxygen in the plasma then has to diffuse to the surface of the sorbent. At the sorbent surface the oxygen can either react immediately with reactive groups on the surface, or dissolve in the polymer matrix (e.g., a fiber or microparticle). Once dissolved in the polymer matrix $O_2$ can react with groups present within the polymer matrix.

Not to be limited by any particular theory, the depletion of $O_2$ from blood can be illustrated as shown in FIG. 5. Release of oxygen from the red blood cells and diffusion of oxygen to the fiber surface happen sequentially. Reaction at the sorbent surface and diffusion and reaction through the polymeric matrix occur in parallel.

Two approximations are assumed for the geometry of a leukocyte filter: First, the leukocyte filter assumed to be a packed bed where:

$$\frac{k}{v^0} = 1.17 \left(\frac{dv^0}{\gamma}\right)^{-0.42} \left(\frac{D}{\gamma}\right)^{\frac{2}{3}}$$

and k=mass transfer coefficient, $v^0$=superficial velocity=350 mL/(50 cm²*30 min)=2.33 mm min⁻¹=3.89×10⁻⁵ m s⁻¹, d=particle diameter (assumed to be fiber diameter)=3.5 μm, $dv^0$=kinematic viscosity=viscosity/density=3.5×10⁻³/1060=3.30×10⁻⁶ m² s⁻¹, D=diffusivity of oxygen in blood=(2.13−0.009 Hct)×10⁻⁹=1.64×10⁻⁹ m² s⁻¹ (at 55% Hct), Thus k=1.98×10⁻⁵ m s⁻¹ or 0.12 cm min⁻¹. Second, the leukocyte filter is assumed to be a capillary bed with flow perpendicular to the fibers.

$$\frac{kd}{D} = 0.80 \left(\frac{dv^0}{\gamma}\right)^{0.47} \left(\frac{\gamma}{D}\right)^{\frac{1}{3}}$$

d=capillary diameter=3.5 μm, D=diffusivity of oxygen in blood (from above) 1.64×10⁻⁹ m² s⁻¹, $v^0$=velocity approaching bed (assume same as superficial velocity), and $dv^0$=kinematic viscosity from above. Thus k=4.12×10⁻⁵ m s⁻¹=0.25 cm min⁻¹. Notably, the two estimates are within a factor of 2 of each other. For the purposes here, The lower value is used as it is more conservative.

The flux of oxygen in the plasma is given by $$J = k\Delta C$$

Where, J=oxygen flux, k=mass transfer coefficient, $\Delta C$=concentration driving force.

For the illustrative purposes, it is assumed that the oxygen concentration at the fiber surface is zero. Practically, this amounts to assuming very rapid surface reaction or very rapid diffusion and reaction through the fibers. This gives the maximum concentration driving force and maximizes the rate of oxygen transfer through the plasma to the surface of the fiber.

Assuming 100 mL oxygen in 350 mL at STP (101325 Pa, 273.15 K).

Using the idea gas law $$\frac{PV}{RT} = n$$

where P, V, R, T and n are pressure (Pa), volume (m³), gas constant (8.314 J mol⁻¹ K⁻¹), temperature (° K) and number of moles (mol) respectively. Thus the total number of moles of oxygen that must be removed in 350 mL of packed red blood cells is 4.46×10⁻³.

Assuming the volume of a leukocyte filter is 50 cm²×2.5 cm=125 cm³ (including fiber volume), in order to process 350 mL in 30 minutes the residence time should be 10.71 or 11 min. Thus, the oxygen flux would be J=1.98×10⁻⁵ m s⁻¹×4.46×10⁻³ (mol $O_2$)/350×10⁻⁶ m³=2.52×10⁻⁴ mol m⁻² s⁻¹.

Assuming a density of fabric in a leukocyte filter is 0.225 g cm⁻³, for a filter volume of 125 cm³ total mass of fabric would be 28.125 g. Assuming a surface density of 20 g m$^{-2}$, total fabric surface area would be 1.4 m$^2$. Thus for a residence time of 11 min and a fabric surface area of 1.4 m$^2$ total amount of O$_2$ that could reach the surface is 2.52×10$^{-4}$ mol m$^{-2}$ s$^{-1}$×1.4 m$^2$×11 min×60 s/min=0.233 mol. Given there is only 4.46×10$^{-3}$ in 350 mL of packed red blood cells it appears diffusion through the plasma will not be limiting.

Some of the assumptions in the simplified analysis above that should be remembered. The maximum concentration driving force has been used by assuming the oxygen concentration in the fiber surface is zero. Such an assumption does not take into account the fact that a leukocyte filter may be a packed bed. For calculation purposes only, the assumption here is that 125 mL is charged and kept in the leukocyte filter for 11 minutes, then discharged then the next 125 mL added etc. In actual operation, the fiber surface near the entrance will be exhausted first and the beginning of an oxygen free region of the sorbent will move down the filter.

The time required to for O$_2$ contained within the red blood cells to be released has not been estimated and is difficult to predict given the variability of human blood, changes in the oxygen hemoglobin dissociation curve with temperature, CO$_2$ etc.

The rate of diffusion through polyethylene therephthalate (PET) can also be considered according to the methods of Li (Li, H., "Kinetics and Mechanisms for the Oxidation Process for Unsaturated Hydrocarbon Modified Scavengers", Dissertation University of Toledo, August 2010). According to Li, oxygen permeability (P) of PET=5 cm$^3$-mil/(day-100 in$^2$-atm). Converting to Si units $$P = \frac{5 \times 10^{-6} \times \frac{1}{1000} \times 2.54 \times 10^{-2}}{24 \times 60 \times 60 \times 100 \times (2.54 \times 10^{-2})^2 \times 101325} =$$

$$2.25 \times 10^{-19} \text{m}^3 \text{m}^{-2} \text{s}^{-1} / (\text{Pa/m})$$

If the oxygen concentration in the PET is assumed to be zero for a fiber is 3.5 μm in diameter and under STP conditions, J=P ΔP/Δx where Δx is 1.75 μm.

Thus J=2.25×10$^{-19}$ m$^3$ m$^{-2}$ s$^{-1}$/(Pa/m)*2666/1.75× 10$^{-6}$=3.4×10$^{-10}$ m$^3$ m$^{-2}$ s$^{-1}$. This is the volumetric flux of oxygen through the film. It is for permeation of oxygen through the fiber when the fiber is exposed to gaseous oxygen at a partial pressure of 20 torr (2666 Pa). Assuming the maximum driving force (i.e., oxygen concentration in the fiber is always zero). Converting to a molar flux, using the ideal gas law, J=4.0×10$^{-10}$ mol m$^{-2}$ s$^{-1}$, assuming 11 min residence time and 1.4 m$^2$ fiber surface area we get 3.7×10$^{-7}$ mol. This compares with 4.46×10$^{-3}$ mol oxygen that is present in the red blood cell concentrate.

Significantly, these calculations indicate that diffusion through the polymeric fibers is an important mass transfer resistance. Based on the assumptions described above, and not being limited by any theory, the amount of oxygen removed would be expected to be several orders of magnitude less than the oxygen present. Thus, if diffusion were to occur through a non-reactive coating on the surface of the fiber, the permeability of the material would need to be more than 4 orders of magnitude higher than PET. Moreover, suitable materials can be selected for the preparation of a macroporous structure based on an analysis of the permeability.

In aspects according to the present disclosure and referring to Table 1, silicone rubber may be used as an alternative to PET for encapsulation or incorporation of oxygen sorbents. In other aspects, materials that have a permeability about 4 orders of magnitude greater than PET are possible polymers to be used.

TABLE 1

Oxygen permeability of silicone rubber [9]

| Polymer | Permeability*10$^9$, cm$^3$*cm/(s*cm$^2$*cmHg) |
|---|---|
| Dimethylsilicone rubber | 60.0 |
| Fluorosilicone | 11.0 |
| Nitrile rubber | 8.5 |
| Natural rubber | 2.4 |
| Polyethylene, low density | 0.8 |
| Butyl rubber | 0.14 |
| Polystyrene | 0.12 |
| Polyethylene, high density | 0.10 |
| Nylon 6 | 0.004 |
| Poly(ethylene terephthalate) | 0.0019 |
| "Teflon" | 0.0004 |

O$_2$/CO$_2$ sorbent materials can be formed into microspheres and then coated with a biocompatible leukocyte binding surface chemistry. These microspheres may then be incorporated into any conventional leukoreduction filer material in a either a layer or random fashion. O$_2$/CO$_2$ present in the pRBC may be transferred to the sorbent material as it flows through the filter structure. Inorganic iron sorbent mixtures can be combined in a polar water containing solution and then added into a nonpolar liquid, forming an emulsion to create the microspheres. An oxidizable polymer can also be added into a polar solvent and then emulsified with a non-polar solution (PVOH) to also form microspheres.

In aspects according to the present disclosure, sorbents may be encapsulated into microspheres. For example, silicones can form self-leveling, adhesive films. Silicone elastomers based on dimethyl silicone polymers that contain polar moieties (polyethylene oxide substituents e.g., Dow Corning® 9011 Silicone Elastomer Blend) and low crosslink density make effective emulsifiers for preparing water-in-silicone emulsions. By modifying the water-in-silicone emulsion, oxygen scavengers can be incorporated into aqueous emulsions of ultra-high molecular weight silicones (Dow Corning® HMW 2220 Non Ionic Emulsion). In certain aspects, the addition of ethylene oxide or propylene oxide polymer chains can aid emulsification during formulation and improve compatibility with polar materials.

In aspects according to the present disclosure, monodispersed micro-beads of polydimethylsiloxane (PDMS) can be created in a microfluidic system using flow-focusing. A PDMS precursor solution may be dispersed into microdroplets within an aqueous continuous phase. These droplets may then be collected and then thermally cured into solid micro-beads. These techniques allow incorporation of oxygen scavengers into the PDMS micro-beads. The flow-focusing mechanism creates droplets of PDMS precursors in an aqueous continuous phase bearing the surfactant, sodium dodecyl sulfate (SDS). See, for example, Jiang et al., "Microfluidic synthesis of monodisperse PDMS microbeads as discrete oxygen sensors," Soft Matter 8:923-926 (2006), herein incorporated by reference in its entirety.

In an aspect of the present disclosure, the silicone elastomer may be Sylgard 184. Sylgard® 184 is a common PDMS elastomer kit from Dow Corning® can be used as the dispersed phase. Sylgard® 184 is composed of two fluids, Part A (base, consisting of vinyl-terminated siloxane oligomers) and Part B (curing agent, consisting of siloxane oligomers and catalyst), that have to be mixed and thermally cured to form the final PDMS polymer. The ratios of Part A and Part B may be adjusted to decrease the viscosity for generating stable droplets. In aspects according to the present disclosure, oxygen scavenging compounds can be directly added to the PDMS precursor solution.

In other aspects, microspheres may be created with coaxial electrohydrodynamic atomization (CEHDA). This process can generate droplets down to 1-2 mm (See, Ganan-Calvo et al., "Current and droplet size in the electrospraying of liquids. Scaling laws," J. Aerosol Sci. 28:249-275 (1997); Jayasinghe et al., "Controlled deposition of nano-particle clusters by electrohydrodynamic atomization," Nanotechnology 15:1519-1523 (2004)). An aqueous solution of oxygen sorbent may be created and pumped through an inner capillary while a PDMS solution is pumped through the outer capillary. A several kilovolt potential difference is applied between the capillary and ground electrode to develop a Taylor Cone (conical shaped liquid meniscus at the capillary outlet). The high charge density creates a thin jet which breaks down into droplets creating the microsphere particles. The resulting microspheres may then be collected and thermally cured.

In other aspects, microspheres can also be formed as taught in Ziemelis, U.S. Pat. No. 4,370,160, issued Jan. 25, 1983, entitled "Process for Preparing Silicone Micro-Particles", or inorganic sorbent can be incorporated into microspheres as described in Morita et al., U.S. Pat. No. 5,387,624, issued Feb. 7, 1997, entitled "Method for The Preparation of a Powder Mixture Composed off Cured Silicone Microparticles and Inorganic Microparticles." The inorganic sorbent can also be blended into the silicone as described in Hottle et al., U.S. Pat. No. 6,210,601, issued Apr. 3, 2001, entitled "Method of Making an Oxygen Scavenging Sealant Composition." Each of these patents are hereby incorporated by reference in their entireties.

In aspects according to the present disclosure, any $O_2$ sorbent material may be formed into microspheres and then coated with a biocompatible leukocyte binding surface chemistry, wherein the microspheres may be incorporated into an $O_2$ and leukoreduction filler material in either a layer or random fashion. In other aspects, any $O_2$ and CO2 sorbent material may be formed into microspheres and coated with a biocompatible leukocyte binding surface chemistry, wherein the microspheres may be incorporated into a $O_2$, $CO_2$ and leukoreduction filler material in either a layer or random fashion. In yet other aspects, $O_2$ sorbent material may be formed into microspheres and then coated with a biocompatible leukocyte and platelet binding surface chemistry, wherein the microspheres may be incorporated into a $O_2$ and platelet leukoreduction filler material in either a layer or random fashion. In other aspects, an $O_2$ and $CO_2$ sorbent material may be formed into microspheres and coated with a biocompatible leukocyte and platelet binding surface chemistry, wherein the microspheres may be incorporated into a combined $O_2$, $CO_2$, platelet and leukoreduction filler material in either a layer or random fashion.

In other aspects, mixtures of microspheres having one or more binding capacities may be used as a sorbent material, either in layers or random fashion. For example, an $O_2$ binding microspheres may be coated with a biocompatible leukocyte binding surface chemistry and mixed with $CO_2$ binding microspheres coated with a biocompatible platelet binding surface chemistry to provide for a combined $O_2$, $CO_2$, leukocyte, and platelet sorbent material. Additional configurations and combinations are included aspects of the present disclosure.

Leukoreduction materials according the present disclosure may be prepared as either filters, fibers or microspheres as discussed. In an aspect, leukocyte reduction filters may be formed as described in Lee et al., U.S. Pat. No. 6,337,026, issued Jan. 8, 2002, entitled "Leukocyte reduction filtration media," using micro-glass fibers. Porous glass fibers containing a sorbent as described above can be used as the scaffolding and then grafted PVA or Silicone can used as a binder to coat the fibers and promote leukocyte adhesion.

In another aspect, melt blown fibers as described in Pall, U.S. Pat. No. 4,925,572, issued May 15, 1990, entitled "Device and method for depletion of the leukocyte content of blood and blood components," can be formed from PBT or PET containing sorbent micro-particles and then incorporated into filter devices as taught in Pall, et al., U.S. Pat. No. 5,229,012, issued Jul. 20, 1993, entitled "Method for depletion of the leucocyte content of blood and blood components," and surface modified as described in Gsell, U.S. Pat. No. 5,443,743, issued Aug. 22, 1995, entitled "Gas plasma treated porous medium and method of separation using same." All of which are herein incorporated by reference in their entireties.

In another aspect, meltblown fibers containing a sorbent as described above can also be surface modified as described in Bonaguidi et al., U.S. Pat. No. 7,775,376, issued Aug. 17, 2010, entitled "Filter for the separation of leukocytes from whole blood or blood preparations, method for production of said filter, corresponding device and use thereof," hereby incorporated by reference in its entirety. In another aspect, the monomers of Bonaguidi et al. may be grated onto a silicone coating instead of polymerized.

In aspects according to the present disclosure, $O_2$ sorbent material may be formed into fibers and then coated with a biocompatible leukocyte binding surface chemistry, wherein the fibers may be incorporated into an $O_2$ and leukoreduction filler material in either a woven or random fashion. In other aspects, an $O_2$ and $CO_2$ sorbent material may be formed into fibers and coated with a biocompatible leukocyte binding surface chemistry, wherein the fibers may be incorporated into a sorbent material in a either a woven or random fashion. In yet other aspects, $O_2$ sorbent material may be formed into fibers and then coated with a biocompatible leukocyte and platelet binding surface chemistry, wherein the fibers may be incorporated into a sorbent material in a either a woven or random fashion. In other aspects, the $O_2$ and $CO_2$ sorbent material may be formed into fibers and coated with a biocompatible leukocyte and platelet binding surface chemistry, wherein the fibers may be incorporated into a sorbent material in a either a woven or random fashion.

In other aspects, mixtures of fibers having one or more binding capacities may be used as a sorbent material, either in woven or random fashion. For example, an $O_2$ binding fiber may be coated with a biocompatible leukocyte binding surface chemistry and mixed with $CO_2$ binding fibers coated with a biocompatible platelet binding surface chemistry to provide for a combined $O_2$, $CO_2$, leukocyte, and platelet sorbent material. In other aspects, the fibers may be woven together to provide for a combined $O_2$, $CO_2$, leukocyte, and platelet sorbent material. Additional configurations and combinations of woven or random fibers have different or overlapping binding capacities are included aspects of the present disclosure.

Fibers according the present disclosure may be solid fibers. In an aspect, solid fibers may be used in the preparation of a sorbent material where the blood flows. As provided above, the fibers may be prepared of $O_2$ binding, $CO_2$ binding, or combined $O_2$ and $CO_2$ binding material and coated with a biocompatible leukocyte binding surface, a biocompatible platelet binding surface, or a combined biocompatible leukocyte and platelet binding surface.

In other aspects according the present disclosure, hollow fibers may be prepared. In an aspect, the hollow fiber may provide for the flow of blood within the lumen of the fiber. In an aspect, the interior wall of the hollow fiber may be coated with a biocompatible material such as a leukocyte binding material, a platelet binding material or a combined leukocyte and platelet binding material. In an aspect, the hollow fiber may be prepared from an $O_2$ binding material. In other aspects, the hollow fiber may be prepared from a $CO_2$ binding material. In yet another aspect, the hollow fiber may be prepared from a combined $O_2$ and $CO_2$ binding material.

In other aspects, the hollow fiber may be prepared from a gas permeable material. In an aspect, the hollow fiber may be filled with the flowing blood in the device. In another aspect the hollow gas permeable fiber may be filled with a sorbent material where the flowing blood contacts the outside of the hollow gas permeable fiber. In an aspect, a hollow gas permeable fiber may be filled with an $O_2$ sorbent material. In other aspects, a hollow gas permeable fiber may be filled with an $CO_2$ sorbent material. In yet another aspect, a hollow gas permeable fiber may be filled with an $O_2$ and a $CO_2$ sorbent material. As provided above, a surface in contact with the blood may be coated with a leukocyte binding material, a platelet binding material or a combined leukocyte and platelet binding material to prepare a bi-component or even tri-component filter.

The fibers according the present disclosure may be prepared as fine denier fiber from, for example, poly(ethylene methacrylate cyclohexenyl methylacrylate) and other polymer particle bends. In some aspects, the fibers may be less than 2 microns in diameter. In an aspect, the fibers may be from 0.5 to 2 microns in diameter. In another aspect, the fibers are greater than 100× the diameter. Fibers of the present disclosure may be prepared by meltblowing. In another aspect, the fibers may be from 3 µm to 60 µm. In yet another aspect, the fibers may be from 4 µm to 40 µm. In some aspects, the fibers may be coated or modified before being formed into a macroporous structure. In other aspects, the fibers may be coated or modified after being formed into a macroporous structure. $O_2/CO_2$ absorbing polymers may be spun into fine denier fibers using conventional methods. These fibers may then formed into a leukoreduction media. The surface chemistry of the fibers may be modified before or after they are formed into a filter structure. These fibers can be made from poly(ethylene methacrylate cyclohexenyl methylacrylate) or other polymer particle bends.

Leukoreduction materials can be formed as a bi-component fiber. These fibers may contain a core of $O_2/CO_2$ absorbing material surrounded by a biocompatible leukocyte binding sheath. In an aspect, fibers may be less than 2 micron diameter.

In an aspect, the leukoreduction materials can be blended with $O_2/CO_2$ absorbing materials and formed into a filter structure. For example, polyolefins (PP, PE, PMP), polyamides (nylon 6, nylon 610, nylon 10, 11, 12), polyesters (PET, PBT) polymers may be blended with an oxygen scavenger, such as Amosorb DFC 4020 in the polymer form and then spun into fibers.

In certain aspects according to the present disclosure, the depletion media may further include a platelet depletion coating. In another aspect, a separate depletion media capable of removing platelets may be mixed with the $O_2$, $CO_2$, and leukocyte reduction media. In an aspect the platelet depletion media may be a fiber. In another aspect, the platelet depletion media may be a microsphere prepared as discussed above. In some aspects, the fiber or microsphere may be surface coated. Exemplary platelet depletion coatings are provided in, for example, in U.S. Pat. Nos. 5,783,094, 7,721,898, 7,775,376, and U.S. Pat. No. 4,880,548.

In other aspects according to the present disclosure, the platelets may be removed by filtration. In an aspect, the blood filter device may include a second membrane capable of excluding platelets. In an aspect, a platelet removing membrane may be disposed between the membrane of the inner chamber and the outer wall so that plasma permeates through the second membrane, enters the outer chamber and exits the housing through said first outlet. In an aspect, the membrane may be an asymmetric polysulfone filter with a 0.5 to 1.0 micron pore size.

The blood filter device of the present disclosure prepares pRBCs and plasma that has been depleted of $O_2$ and leukocytes. In some aspects, the pRBCs and plasma produced by the device are further depleted of $CO_2$ and optionally platelets. In an aspect, the amount of $O_2$ remaining may be measured as the percent saturation of hemoglobin ($sO_2$). Untreated whole blood and whole donor blood has a typical $sO_2$ of about 40%. An $O_2$ depleted pRBC according to the present disclosure has an $sO_2$ of less than 30%. In other aspects, the $sO_2$ is less than 20%. In another aspect, the $sO_2$ of a depleted pRBC may be less than 10%. In aspects with higher $sO_2$, from 5 to 10%, antioxidants may be added to the storage bag. In another aspect, the $sO_2$ may be up to 5%. In an aspect, the blood filter device provides pRBCs with an initial $sO_2$ of 3% or less. In another aspect, the blood filter device provides for an initial $sO_2$ of 2.5%. In another aspect, the blood filter device provides for an initial $sO_2$ of 2%. In yet another aspect, the initial $sO_2$ may be 1.5%. In another aspect, the initial $sO_2$ may be 1% or less. In other aspects, the $sO_2$ may range from 1 to 3.5%. In another aspect, the $sO_2$ may range from 1.5 to 3.5%. In yet another aspect the $sO_2$ may range from 2 to 3.5%. In a further aspect, the $sO_2$ may range from 1.5 to 2.0%.

In certain aspects according to the present disclosure, the blood filter provides for, and may include a $CO_2$ depletion media. In an aspect, the device prepares pRBCs and plasma that has been depleted of $CO_2$. In aspects according the present disclosure, $CO_2$ measurements are expressed as the partial pressure of $CO_2$ of the plasma or pRBCs measured at 37° C. after treatment in the blood filter device. In an aspect, the initial $CO_2$ may be less than 30 mmHg. In another aspect, the initial $CO_2$ may be less than 20 mmHg. In another aspect, the initial $CO_2$ may be less than 10 mmHg. In other aspects according the present disclosure, the $CO_2$ remaining in the plasma, pRBCs or treated blood may be between 5 and 30 mmHg. In an aspect, $CO_2$ remaining in the plasma, pRBCs or treated blood may be between 5 and 40 mmHg. In another aspect, the initial $CO_2$ remaining may be between 2 and 10 mmHg. In other aspects, the initial $CO_2$ remaining may be between 10 and 20 mmHg. In yet other aspects, the initial $CO_2$ may be between 1 and 80 mmHg.

The blood filter of the present disclosure includes and provides for the concentration of RBCs to prepare pRBCs. In an aspect, the hematocrit of the pRBCs may be greater than 35%. In another aspect, the hematocrit of the pRBCs may be 45, 50, 55, 60 or 65%. In yet another aspect, the hematocrit of the pRBCs may be up to 75%. In others aspect, the hematocrit of the pRBCs may be greater than 75%. In some aspects, the hematocrit of the pRBCs may be between 35 and 75%. In a further aspect, the hematocrit of the pRBCs may be between 40 and 60%. The hematocrit of the pRBCs produced by the device of the present disclosure may range from 35 to 45%, 35 to 55%, or 35 to 65%.

The blood filter of the present disclosure includes and provides for the preparation of leukoreduced pRBCs. In an aspect, the number of leukocytes is reduced to a level below 1000 cells/µl. In another aspect, the number of leukocytes is reduced to a level below 100 cells/µl. In yet another aspect, the number of leukocytes is reduced to a level below 10 cells/µl. In an aspect according to the present disclosure, the number of leukocytes remaining after leukoreduction may be from 1 cell to 10 cells/µl. In another aspect, the number of leukocytes remaining may be from 5 to 20 cells/µl. In another aspect, the number of leukocytes remaining may be from 5 to 10 cells/µl, 5 to 50 cells/µl, 5 to 100 cells/µl, 10 to 20 cells/µl, or 5 to 100 cells/µl.

The blood filter of the present disclosure includes and provides for the preparation of platelet depleted pRBCs. In an aspect, the platelet depleted pRBCs of the present disclosure may be reduced by 10 fold or more. In an aspect, the number of platelets in the depleted pRBCs may be about 1000 platelets/µl. In another aspect, the number of platelets remaining may be less than 10,000 platelets/µl. In an aspect the number of platelets remaining may be less than 5,000 platelets/µl. In an aspect, the number of platelets remaining may be 2000 platelets/µl or less. In an aspect, the number of platelets may be from 1000 to 2000 platelets/µl. In another aspect, the number of platelets may be from 1000 to 5000 platelets/µl.

In an aspect of the present disclosure, the blood filter device may have PBT microfibers loaded with iron clay nanoparticles functionalized on the fiber surface for leukocyte and platelet adhesion loaded into the inner chamber and having a membrane of a hydrophilic polyethersulfone/polyvinylpyrrilodone with a 0.45 micron pore size where the inner chamber rotates to prevent laminar flow and blockage of the membrane pores.

A blood filter of the present disclosure includes and provides for the preparation of depleted blood for storage in an anaerobic storage bag. Storage of depleted blood according to the present disclosure under anaerobic conditions decreases storage lesions, decreases iron overload in chronically transfused patients, increases $O_2$ release from hemoglobin and increases the ability of RBCs to enter and perfuse a capillary bed. Exemplary anaerobic storage bags suitable for the storage of depleted blood produced by the methods and devices of the present disclosure are provided in U.S. patent application Ser. No. 12/901,350, filed on Oct. 8, 2010, entitled "Blood Storage Bag System and Depletion Devices with Oxygen and Carbon Dioxide Depletion Capabilities," herein incorporated by reference in its entirety.

In an aspect according the present disclosure, depleted blood stored under anaerobic conditions has fewer storage lesions compared to non-depleted blood stored conventionally. In an aspect, storage lesions may be decreased by 10% or more after 21 days of storage. In another aspect, storage lesions may be decreased by 20% or more after 21 days of storage. In another aspect, storage lesions may be decreased by 30%, 40% or 50% or more after 21 days of storage. In a further aspect, storage lesions may be decreased between 5 and 30% after 21 days of storage. In an aspect, storage lesions may be decreased between 10 and 30% after 21 days of storage. In an aspect, storage lesions may be decreased between 20 and 30% after 21 days of storage. In an aspect, storage lesions may be decreased between 10 and 50% after 21 days of storage. In an aspect, storage lesions may be decreased between 20 and 50% after 21 days of storage. In an aspect, storage lesions may be decreased between 30 and 50% after 21 days of storage.

In an aspect according to the present disclosure, depleted blood stored under anaerobic conditions has decreased iron overload in chronically transfused patients compared to non-depleted blood stored conventionally. In an aspect, iron overload may be decreased by 10% or more after 21 days of storage. In another aspect, iron overload may be decreased by 20% or more after 21 days of storage. In another aspect, iron overload may be decreased by 30%, 40% or 50% or more after 21 days of storage. In a further aspect, iron overload may be decreased between 5 and 30% after 21 days of storage. In an aspect, iron overload may be decreased between 10 and 30% after 21 days of storage. In an aspect, iron overload may be decreased between 20 and 30% after 21 days of storage. In an aspect, iron overload may be decreased between 10 and 50% after 21 days of storage. In an aspect, iron overload may be decreased between 20 and 50% after 21 days of storage. In an aspect, iron overload may be decreased between 30 and 50% after 21 days of storage.

A blood filter of the present disclosure includes and provides for the preparation of leukocyte, oxygen and carbon dioxide blood that has improved storability compared to unprocessed blood. In an aspect, the processed pRBC product produced by a blood filter of the present disclosure have a $pO_2$ of less than 50 mmHg after anaerobic storage for 21 days. In another aspect, the processed pRBC product produced by a blood filter of the present disclosure have a $pO_2$ of less than 25 mmHg after anaerobic storage for 21 days. In another aspect, the processed pRBC product produced by a blood filter of the present disclosure have a $pO_2$ of less than 21 mmHg after anaerobic storage for 21 days. In another aspect, the processed pRBC product produced by a blood filter of the present disclosure have a $pO_2$ of less than 15 mmHg after anaerobic storage for 21 days. In a further aspect, the processed pRBC product produced by a blood filter of the present disclosure have a $pO_2$ of between 10 and 50 mmHg after anaerobic storage for 21 days. In an aspect, the processed pRBC product produced by a blood filter of the present disclosure have a $pO_2$ of between 20 and 50 mmHg after anaerobic storage for 21 days. In an aspect, the processed pRBC product produced by a blood filter of the present disclosure have a $pO_2$ of between 20 and 40 mmHg after anaerobic storage for 21 days.

In an aspect, the processed pRBC product produced by a blood filter of the present disclosure have a $pO_2$ of less than 50 mmHg after anaerobic storage for 42 days. In another aspect, the processed pRBC product produced by a blood filter of the present disclosure have a $pO_2$ of less than 25 mmHg after anaerobic storage for 42 days. In another aspect, the processed pRBC product produced by a blood filter of the present disclosure have a $pO_2$ of less than 21 mmHg after anaerobic storage for 42 days. In another aspect, the processed pRBC product produced by a blood filter of the present disclosure have a $pO_2$ of less than 15 mmHg after anaerobic storage for 42 days. In a further aspect, the processed pRBC product produced by a blood filter of the present disclosure have a $pO_2$ of between 10 and 50 mmHg after anaerobic storage for 42 days. In an aspect, the processed pRBC product produced by a blood filter of the present disclosure have a $pO_2$ of between 20 and 50 mmHg after anaerobic storage for 42 days. In an aspect, the processed pRBC product produced by a blood filter of the present disclosure have a $pO_2$ of between 20 and 40 mmHg after anaerobic storage for 42 days.

In an aspect, a processed pRBC product produced by a blood filter of the present disclosure have an increased level of ATP after storage under anaerobic conditions. In an aspect, a processed pRBC product produced by a blood filter of the present disclosure have an ATP level of greater than 4.0 μmol/gHb after 21 days of storage under anaerobic conditions. In an aspect, a processed pRBC product produced by a blood filter of the present disclosure have an ATP level of greater than 4.1 μmol/gHb after 21 days of storage under anaerobic conditions. In an aspect, a processed pRBC product produced by a blood filter of the present disclosure have an ATP level of greater than 4.2 μmol/gHb after 21 days of storage under anaerobic conditions. In an aspect, a processed pRBC product produced by a blood filter of the present disclosure have an ATP level of greater than 4.3 μmol/gHb after 21 days of storage under anaerobic conditions. In an aspect, a processed pRBC product produced by a blood filter of the present disclosure have an ATP level of greater than 4.4 μmol/gHb after 21 days of storage under anaerobic conditions. In a further aspect, a processed blood product may have an ATP level of between 4.0 to 4.5 μmol/gHb after 21 days of storage under anaerobic conditions. In an aspect, a processed blood product may have an ATP level of between 4.3 to 4.8 μmol/gHb after 21 days of storage under anaerobic conditions. In an aspect, a processed blood product may have an ATP level of between 4.5 to 4.8 μmol/gHb after 21 days of storage under anaerobic conditions.

In an aspect, a processed pRBC product produced by a blood filter of the present disclosure have an increased level of ATP after storage under anaerobic conditions. In an aspect, a processed pRBC product produced by a blood filter of the present disclosure have an ATP level of greater than 3.0 μmol/gHb after 42 days of storage under anaerobic conditions. In an aspect, a processed pRBC product produced by a blood filter of the present disclosure have an ATP level of greater than 3.1 μmol/gHb after 42 days of storage under anaerobic conditions. In an aspect, a processed pRBC product produced by a blood filter of the present disclosure have an ATP level of greater than 3.2 μmol/gHb after 42 days of storage under anaerobic conditions. In an aspect, a processed pRBC product produced by a blood filter of the present disclosure have an ATP level of greater than 3.3 μmol/gHb after 42 days of storage under anaerobic conditions. In an aspect, a processed pRBC product produced by a blood filter of the present disclosure have an ATP level of greater than 3.4 μmol/gHb after 42 days of storage under anaerobic conditions. In a further aspect, a processed blood product may have an ATP level of between 3.5 to 4.5 μmol/gHb after 21 days of storage under anaerobic conditions. In an aspect, a processed blood product may have an ATP level of between 3.5 to 4.8 μmol/gHb after 42 days of storage under anaerobic conditions. In an aspect, a processed blood product may have an ATP level of between 3.5 to 4.8 μmol/gHb after 42 days of storage under anaerobic conditions.

In an aspect, a processed pRBC product produced by a blood filter of the present disclosure have an increased level of 2,3 DPG after storage under anaerobic conditions. In an aspect, a processed pRBC product produced by a blood filter of the present disclosure have a 2,3 DPG level of greater than 1.0 μmol/gHb after 21 days of storage under anaerobic conditions. In an aspect, a processed pRBC product produced by a blood filter of the present disclosure have a 2,3 DPG level of greater than 1.5 μmol/gHb after 21 days of storage under anaerobic conditions. In an aspect, a processed pRBC product produced by a blood filter of the present disclosure have a 2,3 DPG level of greater than 2.0 μmol/gHb after 21 days of storage under anaerobic conditions. In an aspect, a processed pRBC product produced by a blood filter of the present disclosure have a 2,3 DPG level of greater than 3 μmol/gHb after 21 days of storage under anaerobic conditions. In an aspect, a processed pRBC product produced by a blood filter of the present disclosure have a 2,3 DPG level of greater than 4.0 μmol/gHb after 21 days of storage under anaerobic conditions. In a further aspect, a processed blood product may have a 2,3 DPG level of between 2.0 to 7.0 μmol/gHb after 21 days of storage under anaerobic conditions. In an aspect, a processed blood product may have a 2,3 DPG level of between 2.0 to 5.0 μmol/gHb after 21 days of storage under anaerobic conditions. In an aspect, a processed blood product may have a 2,3 DPG level of between 1.0 to 8.0 μmol/gHb after 21 days of storage under anaerobic conditions.

Figure 4:
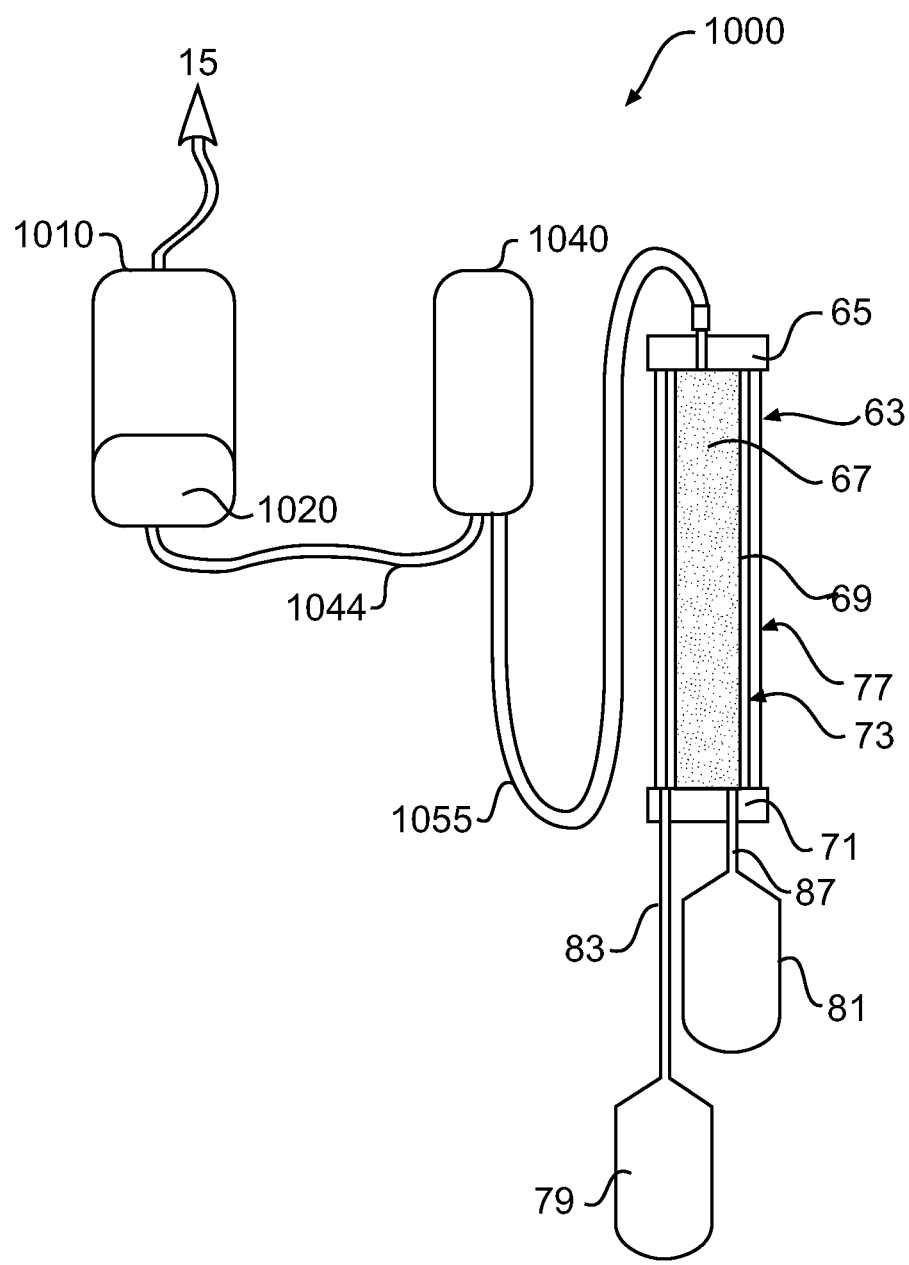
FIG. 4 is a schematic representation of an exemplary system for blood storage incorporating the integrated leukocyte, oxygen/carbon dioxide and depletion and plasma separation filter device according to the present disclosure.

Referring to the drawings and in particular to FIG. 4, an aspect of a disposable blood anaerobic storage system using the leukocyte, oxygen and/or carbon dioxide and plasma depletion filter device 63 is shown and referenced using reference numeral 1000. The blood storage system includes a blood collection bag 1010 for receiving whole blood from donor 15, a leukocyte, oxygen and/or carbon dioxide and plasma depletion filter device 63, and an anaerobic blood storage bag 81. Conduit 1044 connects whole blood from collection bag 1010 and passes it to additive bag 1040 before passing it on to leukocyte, oxygen and/or carbon dioxide and plasma depletion filter device 63 via conduit 1055.

The system of the present disclosure recognizes includes and provides that RBC in storage continue to metabolize. It is desirable to sustain their metabolic rate over time of storage, and yet maintain healthy viable cells that are of high quality for transfusion. The present disclosure uniquely protects essential metabolism, prolongs the shelf life of refrigerated erythrocytes, and provides high quality blood product. Not to be limited by any particular theory, refrigeration reversibly disables the enzymes essential for methemoglobin reduction in vivo, increases the solubility of damaging $O_2$ (almost by a factor of 2) in the environment of the red blood cells, and permits the level of ATP to decrease by diminishing the glycolytic rate (at 4° C. the rate is about 1% of that found at 37° C.). Reduction of red cell ATP concentration results in echinocyte (i.e. an unstable form of red blood cells) formation, increased rates of membrane vesiculation, loss of red cell surface area, and accelerated sequestration by splenic macrophages. Vesiculation continues throughout the cold storage period, is exacerbated by echinocyte formation, and decreases red blood cell survival by decreasing red blood cell membrane area.

Oxygen and/or carbon dioxide removal can be conducted at any temperature that maintains good viability of the RBC. Preferably, oxygen and/or carbon dioxide is removed between about 1° C. and about 37° C. provided that PRBC viability is maintained. Once in the blood storage device of the disclosure, the PRBC can be stored under refrigeration in the manner consistent with common industry practice for storage of blood products, preferably at a temperature between 1° C. and 10° C., and more preferably at about 4° C. Such storage periods range from about 3 to about 20 weeks and longer. Preferred storage periods are about 6 to about 15 weeks duration or longer provided RBC quality is maintained.

In aspects according to the present disclosure, the blood may flow within the fibers of a gas permeable material surrounded by a depletion media. When the blood fluid flows in a parallel layer, there may be little or no lateral mixing and the flow is known as a laminar flow. When in laminar flow, the time necessary for the diffusion of the $O_2$ or $CO_2$ to diffuse from the center of the moving stream of blood fluid to the depletion media greatly increases. To overcome the diffusion barrier created by laminar flow, a turbulent flow of the blood fluid needs to be created. In aspects of the present disclosure in which the depletion media is composed of microspheres or beads, such diffusion barriers are not created and mixing occurs.

In some aspects, the laminar flow of the blood when flowing within a channel may be disrupted. In an aspect, the flow may be disrupted by one or more 'mixing' areas in which blood flowing within fibers is allowed to exit a first set of fibers, mix, and enter a second set of fibers. By way of discontinuous flow, the diffusion gradient that develops within a fluid channel is disrupted.

In another aspect, the laminar flow of blood flowing in a channel may be disrupted by twisting the channel. The fiber geometry can be designed to create Dean Vortices by controlling the Reynolds number fiber curvature and helix torsion as provided for example by Moll et al., "Dean Vortices Applied to Membrane Process Part II: Numerical Approach," Journal of Membrane Science 288 (2007) 312-335, hereby incorporated by reference.

Laminar flow of blood flowing in a channel may be disrupted by externally rotating the channels. In an aspect, an inner chamber having parallel fibers with flowing blood are rotated relative to the outer chamber or device. Such rotation may be induced using a magnetic drive. In an aspect, the rotation of the inner or outer portion of the device may induce Taylor vortices to enhance filtration and mixing. Examples of devices and methods may be found, for example, in Schoendorfer et al., U.S. Pat. No. 4,713,176, issued Dec. 15, 1987, entitled "Plasmapheresis System and Method"; Nakamura et al., U.S. Pat. No. 5,254,248, issued Oct. 19, 1993, entitled "Blood Plasma Separating Apparatus"; Nose et al., U.S. Pat. No. 4,381,775, issued May 3, 1983, entitled "Method and Apparatus for Low Pressure Filtration of Plasma from Blood"; Hodgins et al., U.S. Pat. No. 5,000,848, issued Mar. 19, 1991, entitled "Rotary Filtration Device with Hydrophilic Membrane"; and Kessler et al., U.S. Pat. No. 5,846,427, issued Dec. 8, 1998, entitled "Extra-Luminal Crossflow Plasmapheresis Devices and Method of Use Thereof," each of which are incorporated herein in their entireties.

Prior to transfusion of pRBC to a patient or recipient, various processes can be effected to maximize acceptance of RBC by the recipient and to optimize the condition of the RBC.

In those patients who are either small or whose circulatory systems cannot process a great influx of RBC, the volume of the pRBC must be reduced immediately prior to transfusion. Such patient who may face such an issue are those suffering from congestive heart failure or neonates. Volume reduction can be accomplished using a variety of methods.

When pRBC are stored for a length of time, the pRBC will generally be stored in a blood bag, e.g., blood bags having a hydrophilic membrane compartment in the top ½ of the bag. Depleted pRBC storage bag 81 preferably has a hydrophilic membrane, not shown, having a membrane pore size of less than <1 micron to retain the RBC cells and to prevent them from flowing through. A bag preferably has a sorbent, as discussed above for purposes of continued depletion of oxygen, carbon dioxide, and oxygen and/or carbon dioxide.

A further processing step that is necessary immediately prior to transfusion is the introduction of nitric oxide precursors to the pRBC to enhance vasoregulatory function.

There is increasing awareness that blood transfusion using banked blood is not only providing fully perceived benefits, but in some cases, harmful to some recipients. One of the major reasons behind lower-than-expected efficacy of transfused blood is postulated to be the loss of vasoregulatory function of RBC caused by degradation of nitric oxide (NO) sequestered in hemoglobin (Hb) molecules within RBC. A recent report showed that as short as 3 hours after blood collection, NO in RBC was lost, and its vasoregulatory activity can be restored with addition of NO replenishing compounds. Accordingly, the introduction of nitric oxide precursors to RBCs during storage in blood bag 81, immediately prior to transfusion and after storage will assist the recipient in receiving optimal benefits from the transfusion. NO can be added to RBCs in storage bag 81 using a small bag or cartridge to inject the above materials in the form of a gas or nitrate or other precursor chemical as part of a transfusion set. Because of increased stability of nitric oxide and its precursors in anaerobic conditions, nitric oxide is added to the anaerobic environment of storage bag 81 prior to transfusion, for example. Additionally, nitric oxide precursors can be added in the post-storage Phase C prior to the addition of oxygen before transfusion. The addition of NO requires prior oxygen removal due to its inherent instability in the presence of oxygen. Additionally, nitric oxide preferably should be added immediately before transfusion in the form of NO gas, NO precursor reagents, or nitrite.

Immediately before transfusion, oxygen can be supplied to RBCs to oxygenate hemoglobin. The addition of oxygen must be accomplished during post-storage phase C after gamma and x-ray irradiation and nitric oxide precursor addition, preferably immediately before transfusion at the bedside. The presence of oxygen with the processes of gamma and X-ray irradiation and the addition of nitric oxide are deleterious to the RBCs as discussed above.

The benefits of oxygen removal and or carbon dioxide removal from RBCs before storage in combination with and other therapies has a positive effect on the outcome of the stored RBCs in advance of transfusion.

Packed RBCs' storage life can be measured by the extent of vesicle formation, extent of hemolysis, and total cellular ATP levels. Long storage life is obtained when the membrane vesicle formation is low, hemolysis is low and high ATP levels are sustained, preferably above about 2-3 µmol ATP per g Hb. All of these parameters are measured by the conventional methods known to those of skill in the art. For example, samples of cells can be assayed for the extent of hemolysis by calculating the fraction of supernatant hemoglobin relative to total hemoglobin. To measure ATP levels, for example, RBCs can be assayed for ATP according to the methods described in Technical Bulletins 336-W and 35— (Sigma Chemical Co., St. Louis, Mo.).

As used herein, improved or prolonged shelf life or improved storage of RBCs refers to the preservation of viable RBC for an extended period of time relative to the current standard of about 6 weeks. In most cases, substantial oxygen removal provides RBC with an extended storage life of about 7-15 weeks and, in some conditions, up to 20 weeks or greater, particularly when cells are suspended in the storage solutions provided by the subject disclosure. Storage life can also be prolonged by initially preventing 2,3-DPG feedback inhibition of the RBC glycolytic pathway.

The in vitro parameters measured after storage of RBCs provide a means to measure in vivo survival of RBCs. The conventional means to assess in vivo survival is to determine the percentage of cell survival 24 hours post transfusion in a recipient. Typically in the USA, the average percentage of cell survival needs to be about or better than 75% to provide an acceptable RBC product. The three parameters, vesicle production, extent of hemolysis, and ATP levels, are routinely used individually in the art to predict in vivo cell survival.

Although the present disclosure describes in detail certain aspects, it is understood that variations and modifications exist known to those skilled in the art that are within the disclosure. Accordingly, the present disclosure is intended to encompass all such alternatives, modifications and variations that are within the scope of the disclosure as set forth in the disclosure.

EXAMPLES

Preparation of PVA Grafted Coatings

A 30 mg/mL PVA solution is prepared by dissolving 1.5 g of PVA in 50 mL of deionized water, stirring for 2 h at 90° C. The pH value of the PVA solution is adjusted to pH 1 with 5 mol/L HCl. The PVA solution is applied to an activated silicone surface by simple adsorption. Then 10 mL of 1 mg/mL terephthaldehyde aqueous solution is added to the PVA solution, stirring for 2 h at 80° C. until the PVA is cross linked. mPEG is oxidized with acetic anhydride and dimethylsulfoxide (DMSO) to create an aldehyde terminated PEG (mPEG-CHO). mPEG-grafted PVA surface is prepared by adding the coated microspheres or fibers into a mPEG-CHO DMSO solution, then toluene-4-sulfonic acid is added and then mixed at 70° C. for 4 h, followed by a deionized water wash, and stored in a vacuum desiccator.

Exemplary Aspect A

Figure 6A:
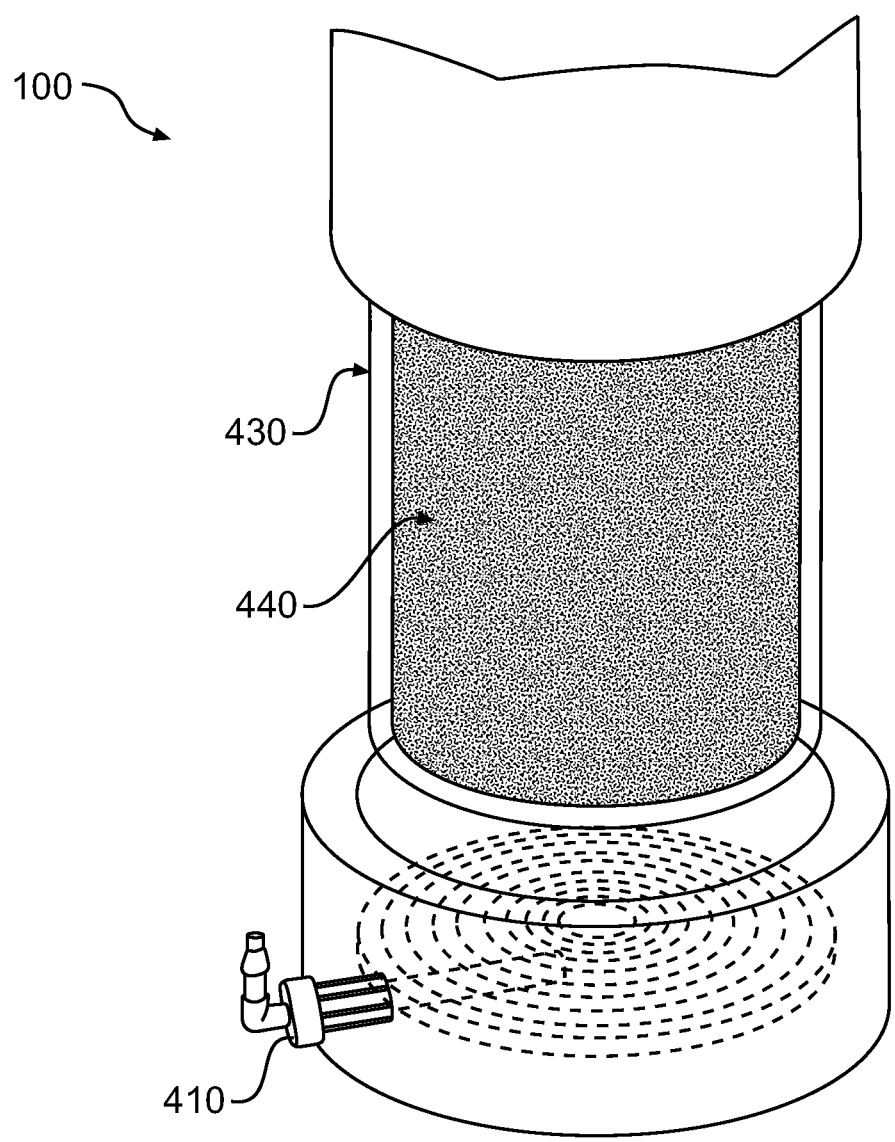
FIGS. 6A and 6B illustrate a partial cross-section view of a whole blood inlet portion of the combination leukoreduction filter and oxygen or oxygen and carbon dioxide depletion device (leukoreduction/$O_2$/$CO_2$ depletion device) according to an exemplary system of FIG. 2.
Figure 6B:
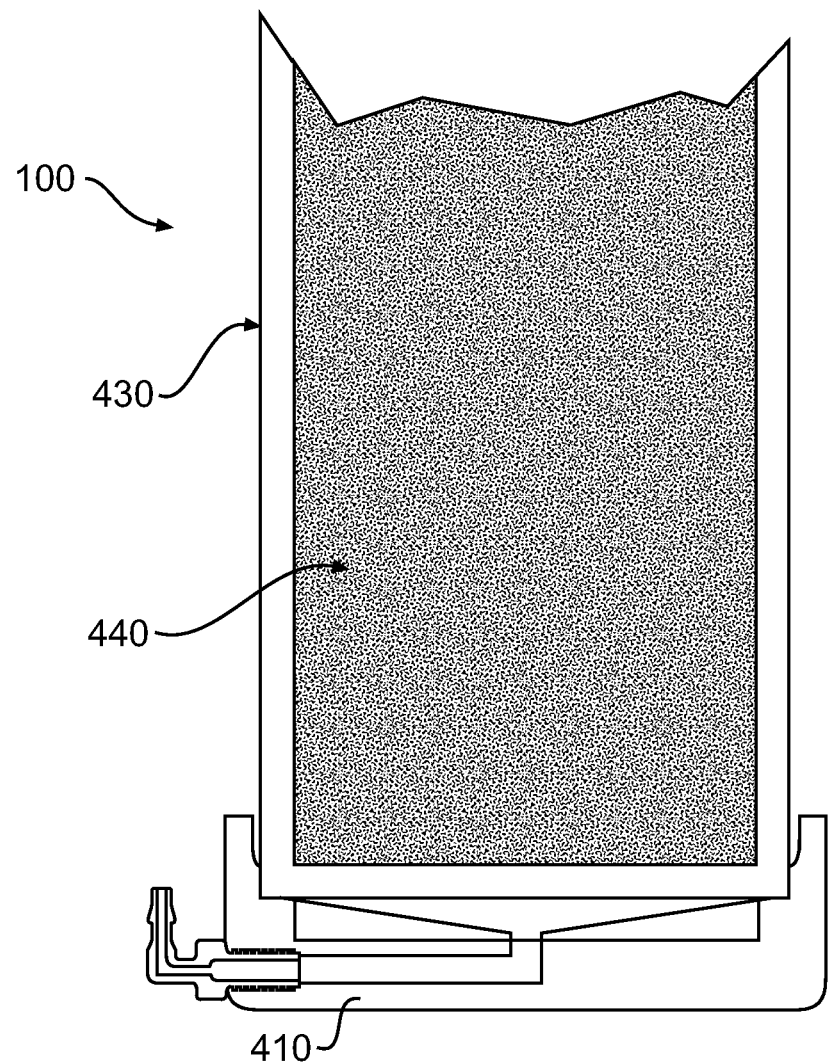

Referring to FIGS. 6A and 6B, a whole blood leukoreduction filter, $O_2$, and $CO_2$ depletion device is shown in partial cross section. Whole blood or whole donor blood flows into the device through a first inlet 410 and is distributed before flowing into the inner chamber 403 containing depletion media 440.

Exemplary Aspect B

Figure 7:
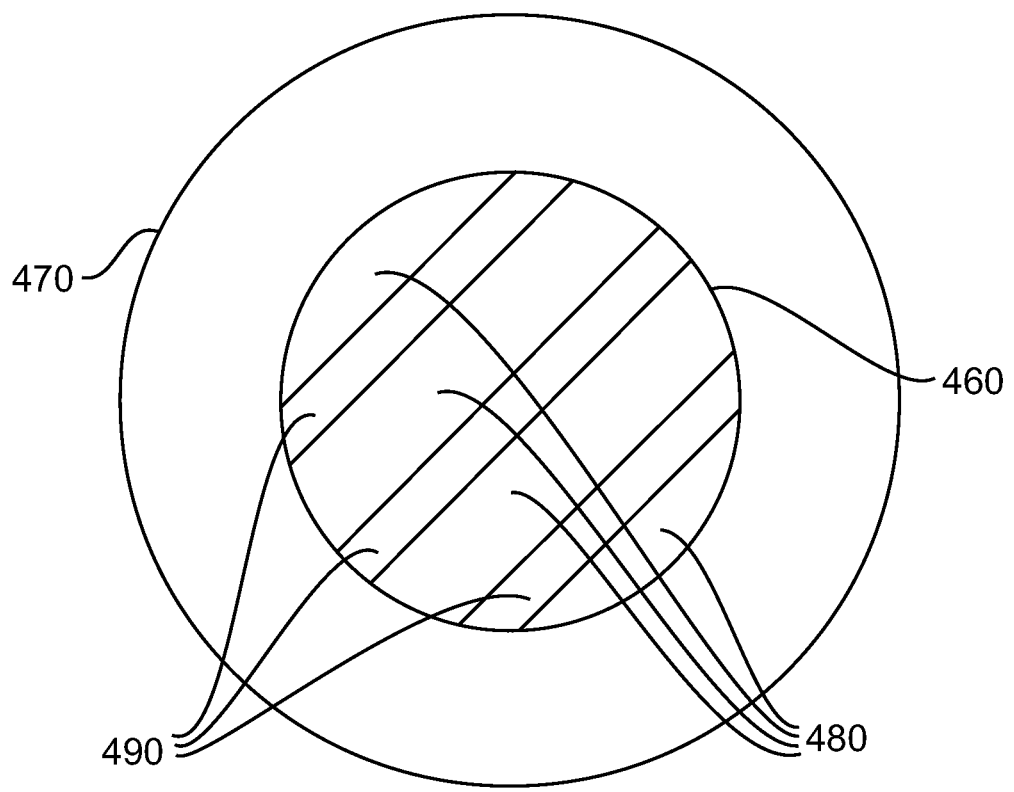
FIG. 7 shows a cross section of an exemplary fiber of leuko-reduction and oxygen/$CO_2$ depletion medium of the device of FIGS. 6A and 6B.

Referring to FIG. 7, inner chamber 403 has a depletion media 480 interposed between hollow fibers 490. The blood flows through the hollow fibers 490 and the $O_2$ and $CO_2$ are absorbed by the depletion media 480.

Exemplary Aspect C

Figure 8A:
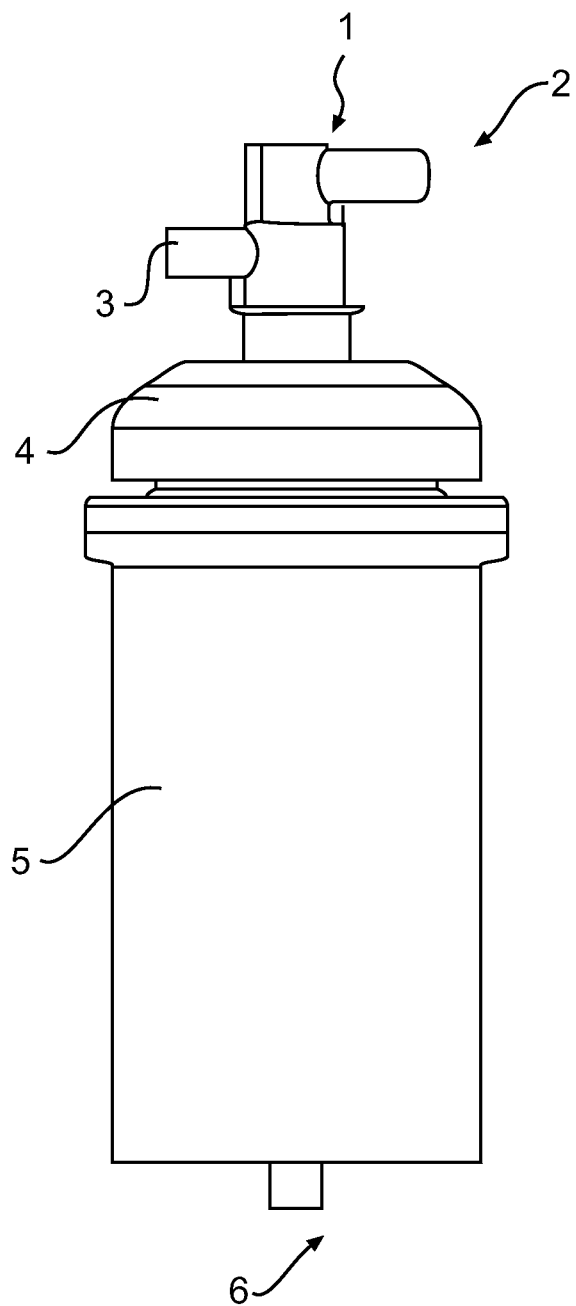
FIG. 8A to 8D illustrate an exemplary Leukocyte/Platelet/Oxygen/Carbon Dioxide Depletion Device according to the present disclosure.
Figure 8B:
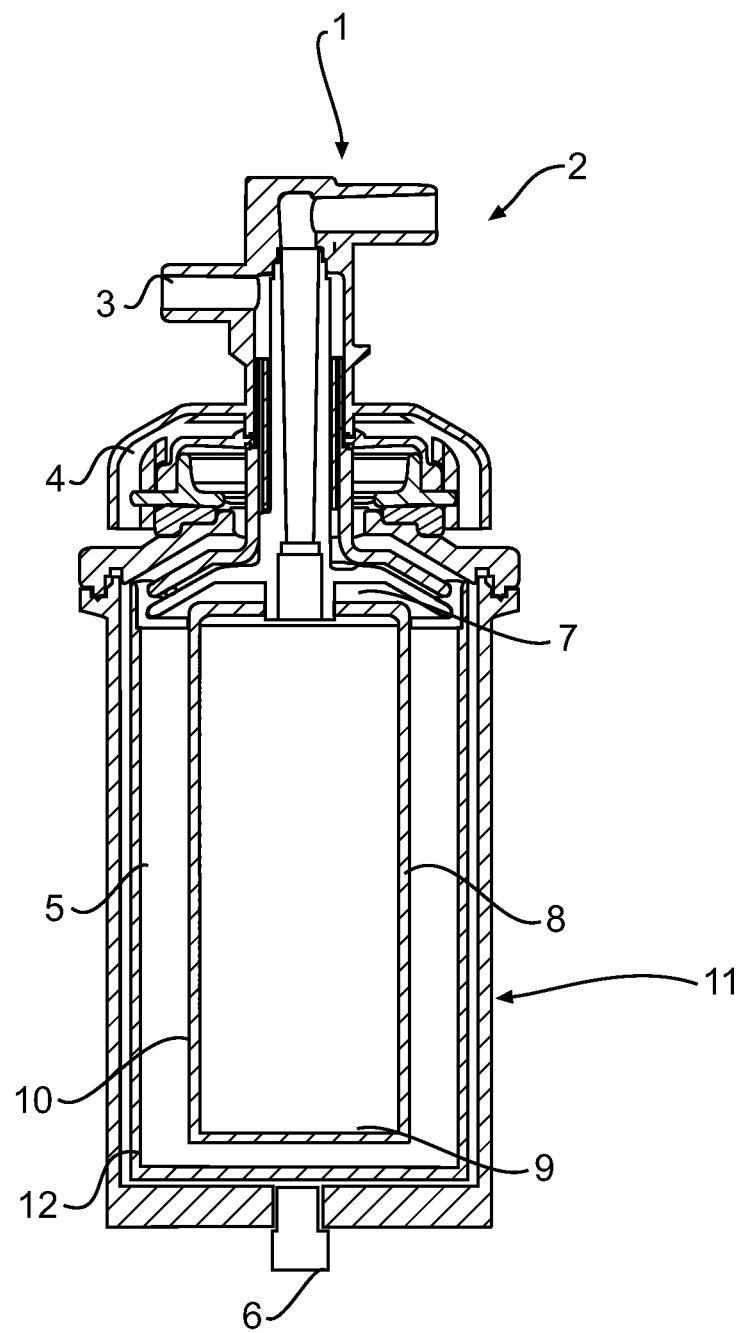

Referring to FIG. 8A to 8D, a Leukocyte/Platelet/Oxygen/Carbon Dioxide Depletion Device 1 is shown. Either whole blood or whole donor blood having an anti-coagulant enters through inlet 2. After passing through the device, the Leukocyte/Platelet/Oxygen/Carbon Dioxide reduced red blood cell concentrate exits from outlet 3 and is collected in a storage bag. FIG. 8B shows a cross section of the integrated device with a rotating seal assembly 4. Blood entering into the device through inlet 2 is distributed to the inner chamber (plasma depletion chamber 10) having Leukocyte/Platelet/Oxygen/Carbon dioxide depletion media 8 through a blood inlet distribution chamber 7. By rotating the inner chamber (Leukocyte/Platelet/Oxygen/Carbon dioxide depletion chamber 5) Taylor Vortices create turbulence and decrease the diffusion time that is increased due to laminar flow. The plasma is filtered through a membrane capable of separating plasma from blood (plasma filter 11) and the plasma exits the device through Leukocyte/Platelet/Oxygen/Carbon dioxide depleted Plasma outlet 6 after collecting plasma collection chamber 12. The Leukocyte/Platelet/Oxygen/Carbon dioxide depleted blood passes to an outlet distribution chamber 9 and flows out through outlet 3.

Figure 8C:
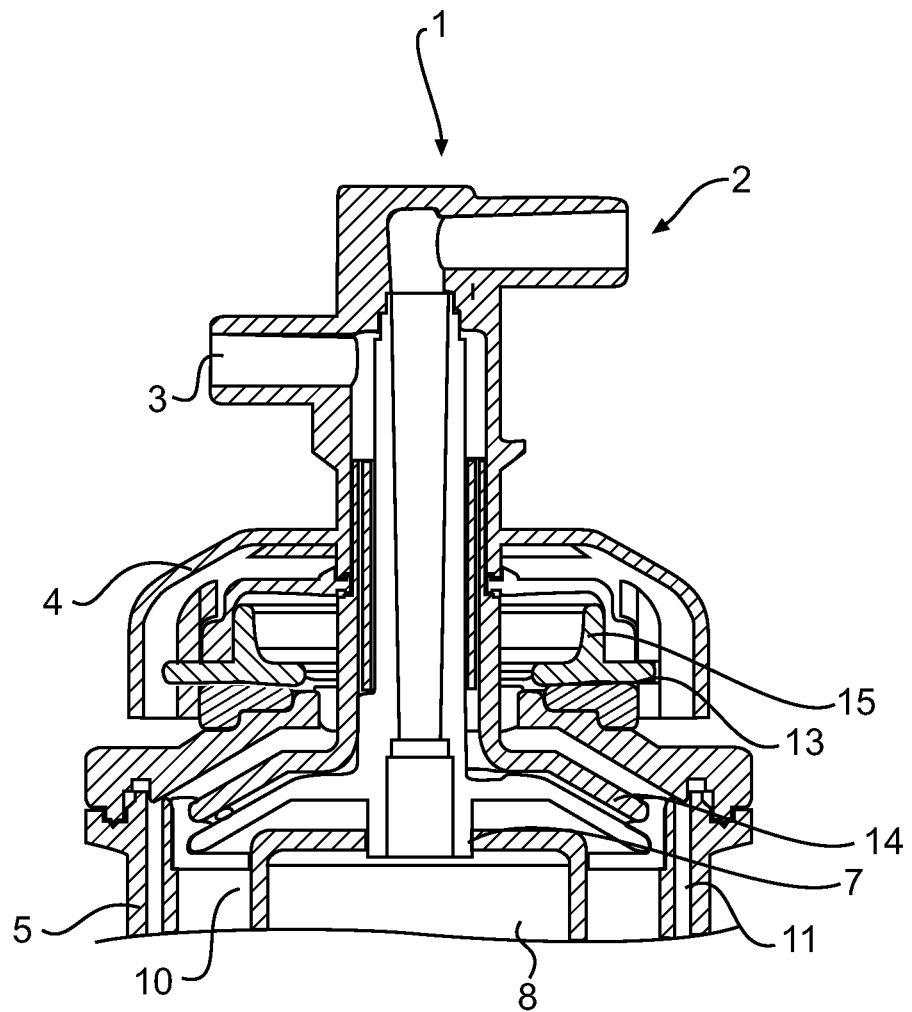
Figure 8D:
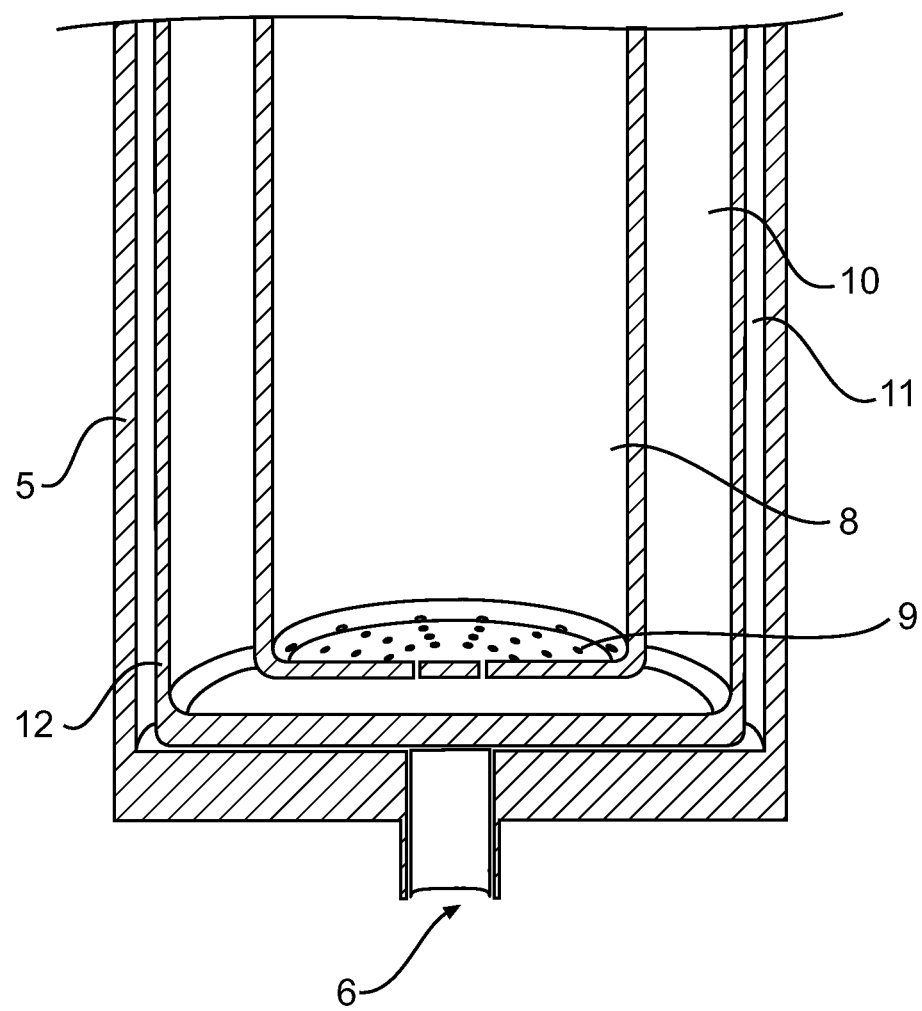

FIG. 8C shows a enhanced cross-sectional view of the depletion device 1. FIG. 8C shows rotary seal 13 that provides for the rotation of the inner chamber 10. An elastomeric bellows 15 provides a downward force on the top ceramic portion of the seal against the lower carbon seal that create a hermetic seal.

Anti-coagulated whole blood flows in through the stationary (non-rotating) blood inlet port (2). The driving force for the flow can be supplied by gravity or a pump or any means capable of creating blood flow in a system from 2-200 ml/min. Blood flows into the inlet port and then into the blood inlet distribution chamber (7). The inlet distribution chamber distributes the blood to the top section of the Leukocyte/Platelet/Oxygen/Carbon dioxide depletion media chamber (8). The whole blood flows down through a bed of Leukocyte/Platelet/Oxygen/Carbon dioxide depletion media contained in the chamber. The media in the chamber adsorbs white blood cells (leukocytes) and platelets and reacts with oxygen and carbon dioxide. When the blood reached the bottom of the media bed, leukocytes are reduced to a level below 10 cells/µl, platelets are reduced down to 1000 platelets/µl, oxygen is reduced down to <1% $SO_2$ and Carbon Dioxide is controlled to levels between 5-40 mmHg. At the bottom of the media bed the depleted red blood cells enter the blood outlet distribution chamber (9) and flow into plasma depletion chamber (10). The plasma depletion chamber is a stationary chamber with the inner wall defined by the stationary Leukocyte/Platelet/Oxygen/Carbon dioxide depletion media chamber and the outer wall consists of a rotating plasma filter wall (11). The rotating plasma filter wall is attached to a rotating seal assembly (4) which consist of a rotary seal comprised of carbon/ceramic lapped components (13) held together via an elastomeric bellows (15). The tangential flow and vortices create a shear effect on the surface of the plasma membrane to prevent red cell cake formation allowing the plasma to permeate through the plasma filter into the plasma collection chamber (12). The Leukocyte/Platelet/Oxygen/Carbon dioxide depletion plasma then exits the plasma collection chamber via a plasma outlet (6) which is coupled to a stationary tube with a rotary seal.

What is claimed is:

1. A method for processing blood, comprising:
passing said blood through a blood filter device comprising:
   a housing comprising an outer wall, a first inlet, a first outlet and a second outlet;
   a membrane which is capable of separating plasma from said blood, wherein said membrane forms at least one inner chamber within said housing and said blood enters said at least one inner chamber of said blood filter device through said first inlet;
   a leukocyte and oxygen depletion media disposed within said at least one inner chamber, said leukocyte and oxygen depletion media is capable of depleting leukocytes and oxygen from said blood; and
   an outer chamber disposed between said outer wall and said membrane,
separating said plasma from said blood by permeating through said membrane, wherein said plasma enters said outer chamber and exits said housing via said first outlet; and depleting oxygen, leukocytes and plasma from said blood, whereby oxygen, leukocytes and plasma depleted blood exits said housing via said second outlet as packed red blood cells (pRBCs).

2. The method according to claim 1, further comprising depleting $CO_2$ from said blood, and wherein said depletion media is also capable of depleting $CO_2$ from said blood.

3. The method according to claim 1, further comprising depleting platelets from said blood, and wherein said depletion media is also capable of depleting platelets from said blood.

4. The method according to claim 1, further comprising rotating at least one inner chamber relative to said outer chamber.

5. The method according to claim 4, wherein said rotating creates vortices in said at least one inner chamber.

6. The method according to claim 1, wherein said pRBCs have an $O_2$ saturation of 3% or less.

7. The method according to claim 2, wherein said pRBCs have a $pCO_2$ of less than 30 mmHg.

8. The method according to claim 1, wherein said pRBCs have a hematocrit of greater than 35%.

9. The method according to claim 1, wherein said membrane is at least one membrane formed from at least one material selected from the group consisting of: PVDF rendered hydrophilic, nylon, cellulose esters, polysulfone, polyethersulfone, polypropylene rendered hydrophilic, and polyacrylonitrile.

10. The method according to claim 1, wherein said membrane is 25 to 250 microns thick.

11. The method according to claim 1, wherein said membrane has a pore size of less than 2 microns.

12. The method according to claim 1, wherein said leukocyte and oxygen depletion media comprises a macroporous structure comprising an oxygen sorbent material and a leukoreduction material.

13. The method according to claim 12, wherein said macroporous structure further comprises a $CO_2$ sorbent material, and wherein said $CO_2$ sorbent material is a metal oxide or metal hydroxide.

14. The method according to claim 12, wherein said macroporous structure is an oxygen sorbent material coated with a biocompatible leukocyte binding surface chemistry.

15. The method according to claim 12, wherein said macroporous structure has a feature selected from the group consisting of a mean flow pore of between 10 and 30 microns, a surface area of at least $5 \times 10^3$ $cm^2$/gram media, and a combination thereof.

16. The method according to claim 12, wherein said macroporous structure comprises a structure selected from the group consisting of:
 a. microspheres coated with a biocompatible leukocyte binding surface chemistry, wherein said microspheres are then incorporated into a leukoreduction filler material;
 b. layers of microspheres;
 c. one or more fibers; and
 d. one or more fibers formed into a filter structure.

17. The method according to claim 16, wherein said one or more fibers are formed from at least one material selected from the group consisting of poly(ethylene methacrylate cyclohexenyl methylacrylate), a polyolefin, a polyamide, a polyester, ethylene/vinyl cyclohexene copolymer (EVCH), and combinations thereof.

18. The method according to claim 16, wherein said one or more fibers comprise fibers selected from the group consisting of:
 a. a leukoreduction fiber and an oxygen sorbent fiber;
 b. a combined leukoreduction binding and an oxygen depletion fiber;
 c. a $CO_2$ depletion fiber;
 d. an oxygen sorbent fiber surrounded by biocompatible leukocyte binding fibers; and
 e. an oxygen sorbent fiber and a carbon dioxide sorbent fiber surrounded by biocompatible leukocyte binding fibers.

19. The method according to claim 12, wherein said leukoreduction material is at least one polymer selected from the group consisting of: polyolefins, polyamides, polyesters, and other polymers which may be blended with an oxygen scavenger the polymer form and then spun into fibers.

20. The method according to claim 1, wherein said passing is performed at a flow rate of at least 3 ml/minute.

* * * * *